United States Patent
Cui et al.

(10) Patent No.: US 10,858,389 B2
(45) Date of Patent: Dec. 8, 2020

(54) SOLUTION PHASE METHOD FOR PREPARING ETELCALCETIDE

(71) Applicant: Amgen Inc., Thousand Oaks, CA (US)

(72) Inventors: Sheng Cui, Lexington, MA (US); Krishnakumar Ranganathan, Thousand Oaks, CA (US); Richard Crockett, Thousand Oaks, CA (US); Ying Chen, Newbury Park, CA (US); Aleksander Swietlow, San Pedro, CA (US); Kevin Crossley, Thousand Oaks, CA (US); Yun Shi, Newbury Park, CA (US); Karel Decroos, Ghent (BE); Etienne Moniotte, Vilvoorde (BE)

(73) Assignee: Amgen Inc., Thousand Oaks, CA (US)

( * ) Notice: Subject to any disclaimer, the term of this patent is extended or adjusted under 35 U.S.C. 154(b) by 372 days.

(21) Appl. No.: 15/561,009

(22) PCT Filed: Mar. 25, 2016

(86) PCT No.: PCT/US2016/024308
§ 371 (c)(1),
(2) Date: Sep. 22, 2017

(87) PCT Pub. No.: WO2016/154580
PCT Pub. Date: Sep. 29, 2016

(65) Prior Publication Data
US 2018/0079777 A1    Mar. 22, 2018

Related U.S. Application Data

(60) Provisional application No. 62/138,903, filed on Mar. 26, 2015.

(51) Int. Cl.
| | | |
|---|---|---|
| *C07K 1/02* | (2006.01) | |
| *C07K 7/06* | (2006.01) | |
| *C07K 1/18* | (2006.01) | |
| *C07K 5/083* | (2006.01) | |
| *C07K 5/11* | (2006.01) | |

(52) U.S. Cl.
CPC ............... *C07K 1/026* (2013.01); *C07K 1/18* (2013.01); *C07K 5/081* (2013.01); *C07K 5/1019* (2013.01); *C07K 7/06* (2013.01)

(58) Field of Classification Search
CPC ........ C07K 1/026; C07K 1/1072; C07K 1/18; C07K 5/081; C07K 5/1019; C07K 7/06
See application file for complete search history.

(56) References Cited

FOREIGN PATENT DOCUMENTS

| WO | WO 2001/005757 A2 | 1/2001 |
| WO | WO 2011/014707 A2 | 2/2011 |
| WO | WO 2014/210489 A1 | 12/2014 |
| WO | WO 2016/154580 A1 | 9/2016 |

OTHER PUBLICATIONS

Califano*, J. C, Concept and Synthetic Approach for a Kilogram Scale Synthesis of Octa-D-Arginine Amide Nonahydrochloride Salt, Peptides for Youth pp. 205-206, 2009.*
Alberico et al., "Use of the Npys thiol protection in solid phase peptide synthesis. Application to direct peptide-protein conjugation through cysteine residues", Int. J. Pept. Protein Res., vol. 34, No. 2, pp. 124-128 (1989).
Harris et al., "Studies on deprotection of cysteine and selenocysteine side-chain protecting groups", J. Peptide Sci., vol. 13, No. 2, pp. 81-93 (2007).
International Search Report and Written Opinion from International Application No. PCT/US2016/024308 dated Jun. 3, 2016, application now published as International Publication No. WO2016/154580 on Sep. 29, 2016.
Okumura et al., "A chemical method for investigating disulfide-coupled peptide and protein folding", FEBS J., vol. 279, No. 13, pp. 2283-2295 (2012).

* cited by examiner

*Primary Examiner* — James H Alstrum-Acevedo
*Assistant Examiner* — Erinne R Dabkowski
(74) *Attorney, Agent, or Firm* — McDermott Will & Emery LLP; Judy M. Mohr

(57) ABSTRACT

The instant disclosure is directed to solution phase fragment coupling methods for preparing etelcalcetide and its pharmaceutically acceptable salts.

19 Claims, 11 Drawing Sheets etelcalcetide DS

Ac-D-Cys(H-L-Cys-OH)-D-Ala-D-Arg-D-Arg-D-Arg-D-Ala-D-Arg-NH2

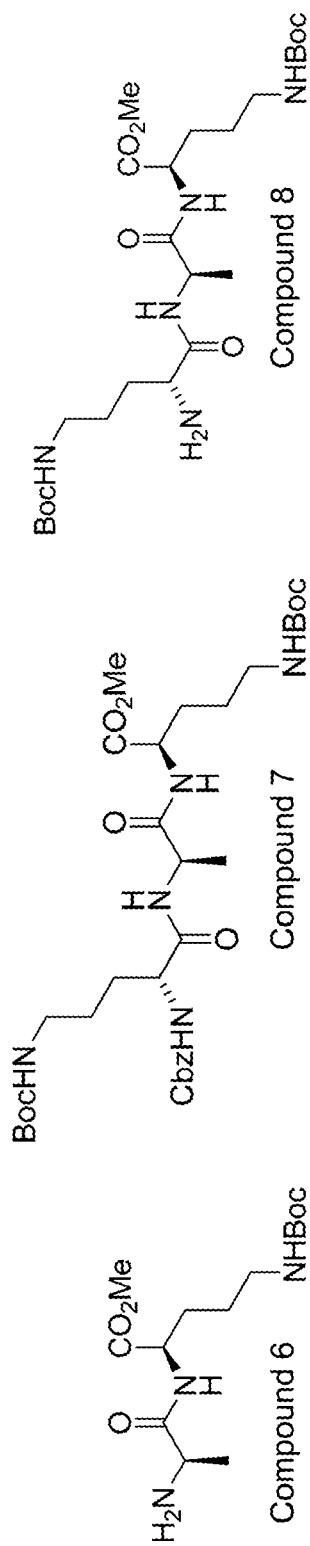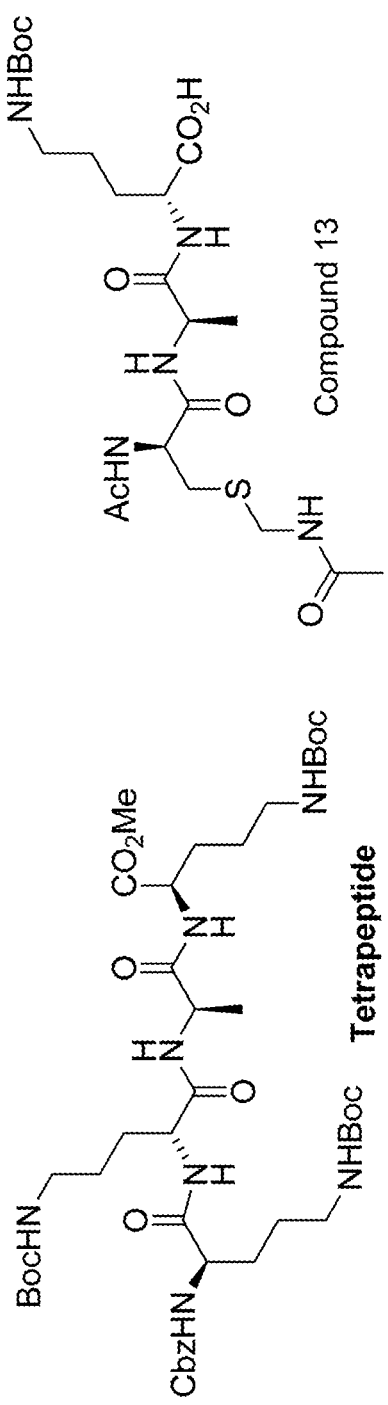
FIG. 8A
FIG. 8B
FIG. 8C
FIG. 8D
FIG. 8E

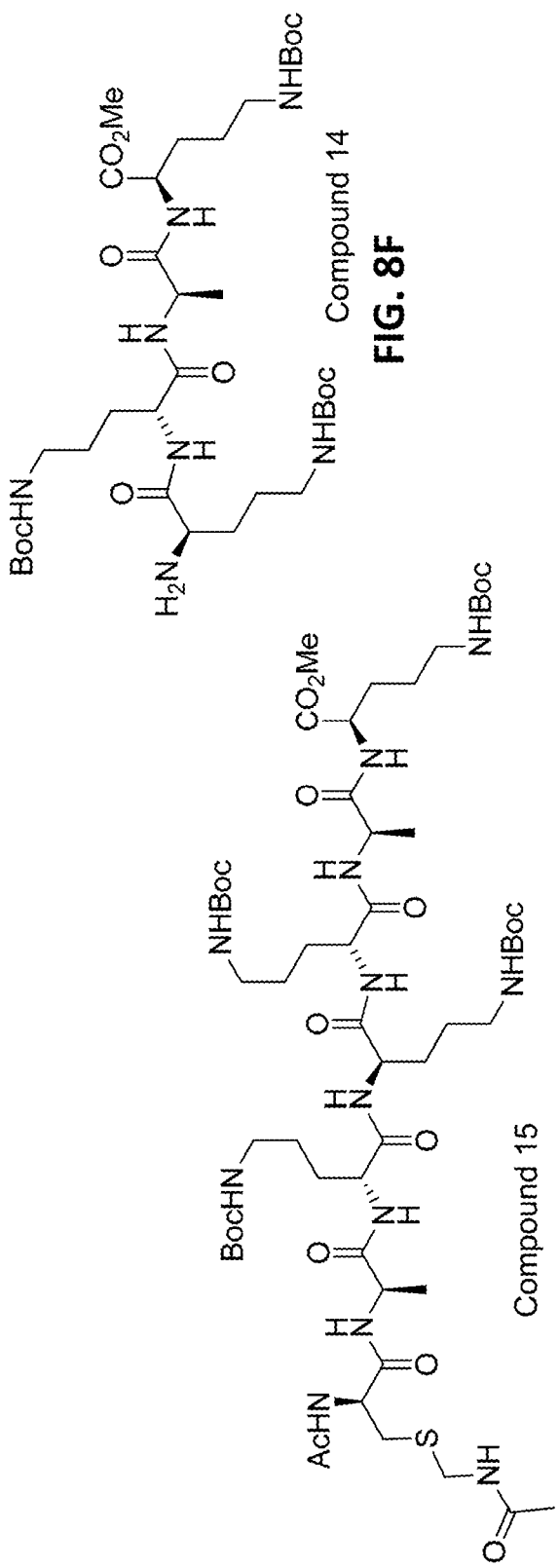
FIG. 8F Compound 14
FIG. 8G Compound 15
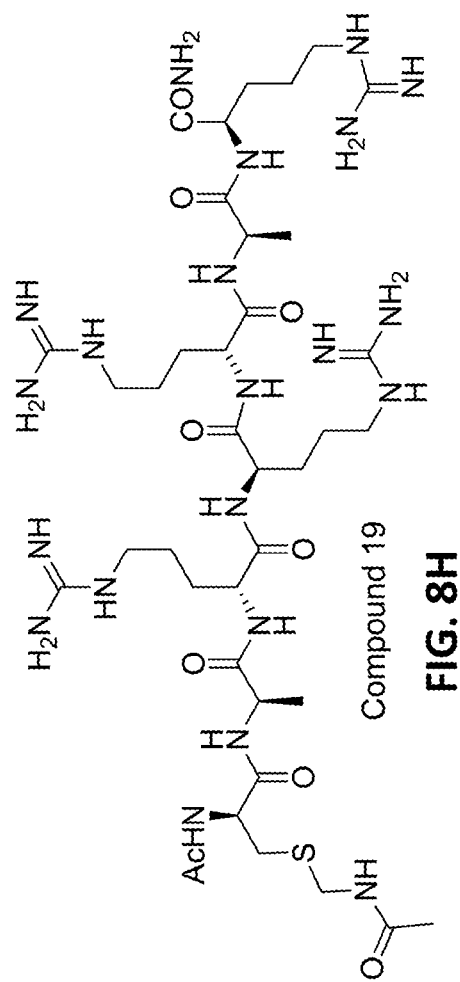
FIG. 8H Compound 19

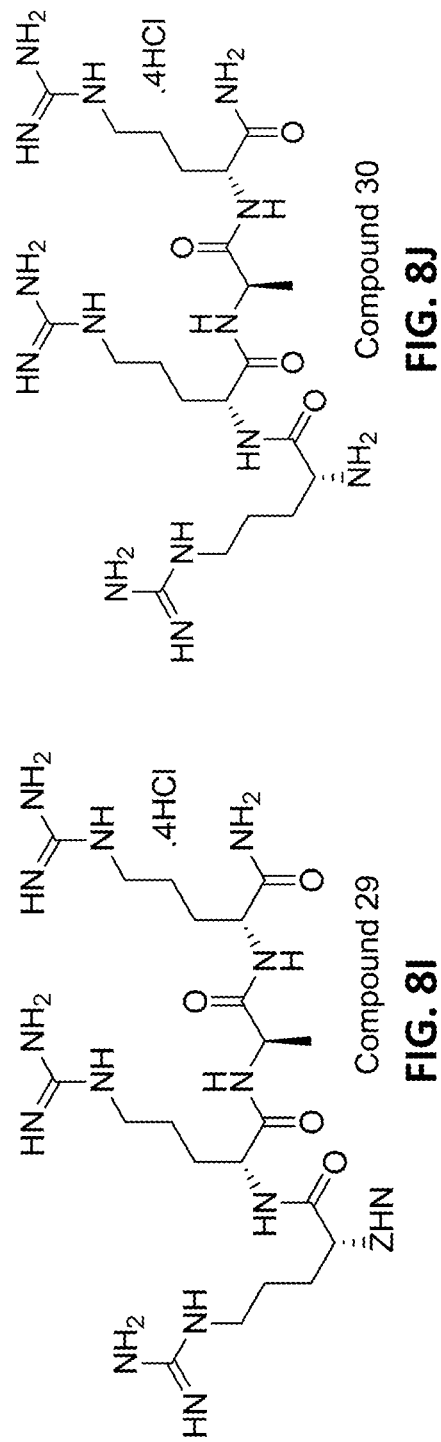
FIG. 8J Compound 30
FIG. 8I Compound 29
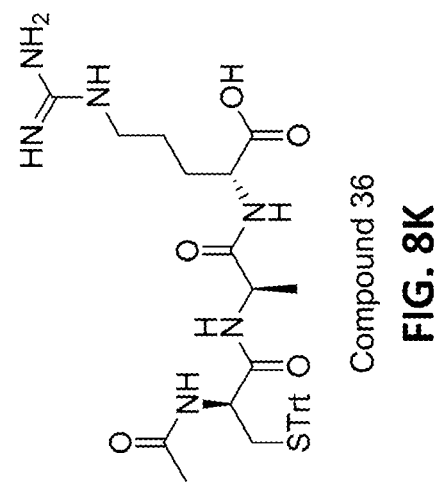
FIG. 8K Compound 36

SOLUTION PHASE METHOD FOR PREPARING ETELCALCETIDE

CROSS-REFERENCE TO RELATED APPLICATIONS

This application is a U.S. National Stage of International Patent Application No. PCT/US2016/024308, filed Mar. 25, 2016, which claims the benefit of priority of U.S. Provisional Patent Application No. 62/138,903, filed Mar. 26, 2015, the contents of which are incorporated herein by reference in their entirety.

FIELD

The present disclosure relates generally to the field of polypeptide synthesis, and more particularly, to the solution phase synthesis of etelcalcetide (formerly known as AMG 416 or velcalcetide) or a pharmaceutically acceptable salt thereof.

BACKGROUND

Etelcalcetide is a synthetic, eight amino-acid selective peptide agonist of the calcium sensing receptor. Etelcalcetide is effective in decreasing parathyroid hormone levels in vivo, and is useful, for example, in treating hypercalcemia or hyperparathyroidism. See, e.g., Walter, S., et al., *J. Pharmacol Exp Ther*, 2013, August: 346(2):229-40. Etelcalcetide is currently being developed for intravenous use in the treatment of secondary hyperparathyroidism (SHPT) in hemodialysis patients with chronic kidney disease—mineral and bone disorder (CKD-MBD); the product will be referred to under the tradename Parsabiv™.

The hydrochloride salt of etelcalcetide has the chemical structure:

Compound 20

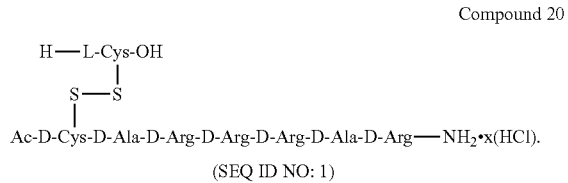

Ac-D-Cys-D-Ala-D-Arg-D-Arg-D-Arg-D-Ala-D-Arg—NH$_2$•x(HCl).

(SEQ ID NO: 1)

The main chain of etelcalcetide, also referred to herein as the backbone of etelcalcetide, possesses seven amino acids, all in the D-configuration, while the side-chain cysteine residue (H-L-Cys-OH) is in the L-configuration. The molecular formula of etelcalcetide (free base) is: $C_{38}H_{73}N_{21}O_{10}S_2$, and has a calculated average molecular mass of 1048.3 Da.

Etelcalcetide and a method for its preparation are described in International Pat. Publication No. WO 2011/014707, which is incorporated herein by reference. Etelcalcetide is traditionally assembled by solid-phase synthesis from the corresponding Fmoc-protected D-amino acids. Following assembly of the main chain by sequential coupling and cleavage from a suitable resin support (i.e., solid phase peptide synthesis), the main chain is treated with a solution of trifluoroacetic acid in the presence of dipyridyldisulfide to form the corresponding activated backbone, which is then treated with L-Cys-OH in water to provide etelcalcetide. The resulting product is then typically purified by reverse-phase high pressure liquid chromatography (RP-HPLC), and isolated as a TFA salt by lyophilization. The TFA salt is then converted to a pharmaceutically acceptable salt such as a hydrochloride salt by carrying out a salt exchange process, e.g., by ion exchange chromatography, optionally followed by purification, for example by reverse phase liquid chromatography or reverse osmosis.

In contrast to the conventional solid phase synthesis described generally above, the instant disclosure provides solution-phase methods for preparing etelcalcetide. The methods provided herein possess several advantages over traditional solid phase syntheses, including but not limited to, low raw materials costs, ease of purification of process intermediates, ease of fragment assembly, high chiral purity, and adaptability to commercial scale-up, among others, to be described in greater detail below.

SUMMARY

Provided herein are solution phase methods for preparing intermediates of etelcalcetide, as well as for preparing etelcalcetide and its pharmaceutically acceptable salts. Generally, the methods comprise solution phase fragment coupling to form the main heptapeptide chain of etelcalcetide, followed by introduction of the L-cysteine side chain via disulfide bridge formation.

More particularly, in a first aspect, provided herein is a method for preparing etelcalcetide or a precursor thereof, the method comprising (i) coupling in solution phase a protected N-terminal tetrapeptide fragment of etelcalcetide comprising D-ornithine(s) in place of D-arginine(s) with a protected tripeptide fragment of etelcalcetide to form a protected heptapeptide precursor of etelcalcetide comprising a terminal D-cysteine.

In one embodiment related to the first aspect, the protected N-terminal tetrapeptide fragment of etelcalcetide has a sequence of SEQ ID NO:2, H-D-Orn(Boc)-D-Orn(Boc)-D-Ala-Orn(Boc)-OMe, (Compound 14). In one or more related embodiments, the protected N-terminal tetrapeptide fragment of etelcalcetide is a solid. In yet one or more further embodiments, the protected N-terminal tetrapeptide fragment of etelcalcetide is a crystallizable solid. The preparation of a solid, optionally crystallizable/crystalline, intermediate such as an N-terminal tetrapeptide fragment of etelcalcetide or any other fragment of etelcalcetide, is particularly beneficial, since it provides the opportunity for purification by solids isolation, e.g., by precipitation or by crystallization, rather than utilizing conventional time- and solvent-consuming chromatographic methodologies.

In yet one or more further embodiments related to the first aspect, the tripeptide fragment has a sequence of SEQ ID NO:3, Ac-D-Cys(Acm)-D-Ala-D-Orn(Boc)-OH), (Compound 13), and the protected heptapeptide precursor of etelcalcetide has a sequence of SEQ ID NO:4, Ac-D-Cys(Acm)-D-Ala-D-Orn(Boc)-D-Orn(Boc)-D-Orn(Boc)-D-Ala-Orn(Boc)-OMe (Compound 15).

In yet one or more additional embodiments related to the first aspect, the tripeptide fragment is a solid. In yet one or more related embodiments, the tripeptide fragment is a crystallizable solid.

In yet one or more further embodiments, coupling is carried out in an organic solvent to provide a reaction mixture, and the method further comprises adding water to the reaction mixture to precipitate the protected heptapeptide precursor of etelcalcetide.

In yet one or more further embodiments related to the foregoing, the method further comprises (ii) removing the ornithine δ-amino protecting groups from the protected heptapeptide precursor of etelcalcetide, and (iii) guanitinylating the deprotected heptapeptide precursor of etelcalcetide to thereby replace the ornithine residues with arginine to form an intermediate having a sequence of SEQ ID NO:5 (Compound 19).

In one or more further embodiments, the method further comprises (iv) coupling the terminal D-cysteine of the intermediate formed in step (iii) with L-cysteine via formation of a disulfide bond to form etelcalcetide (SEQ ID NO:1, Compound 20).

In yet one or more additional embodiments of the method according to the first aspect, the method further comprises, prior to coupling step (i), (a) preparing in solution phase the protected N-terminal tetrapeptide fragment of etelcalcetide. In one or more embodiments related to the foregoing, the protected N-terminal tetrapeptide of etelcalcetide is prepared via a continuous solution phase process. More particularly, in one or more further embodiments, the preparing step (a) comprises:

(a-i) coupling a urethane protected N-carboxyanhydride (UNCA) of ornithine with a dipeptide having SEQ ID NO:6 (Compound 6) to form a protected tripeptide, (a-ii) deprotecting the tripeptide to form a deprotected tripeptide, and (a-iii) coupling the deprotected tripeptide to a urethane protected N-carboxyanhydride of ornithine to form the protected N-terminal tetrapeptide fragment of etelcalcetide. Exemplary fragments corresponding to the foregoing include a fully protected tripeptide of step (a-i) having SEQ ID NO:7 (Compound 7) and a partially deprotected tripeptide having SEQ ID NO:8 (Compound 8).

In one or more embodiments related to the foregoing, the preparing step results in formation of a gaseous by-product.

In yet one or more additional embodiments, the urethane-protected N-carboxyanhydride of ornithine is a benzyloxycarbonyl-protected N-carboxyanhydride of protected D-ornithine.

In yet one or more further embodiments, each of the coupling steps (a-i) and (a-iii) is carried out in tetrahydrofuran.

In yet another one or more embodiments pertaining to step (a) or sub-steps thereof, the solution phase comprises an organic solvent selected from the group consisting of ethers, esters, aromatic hydrocarbons, and chlorinated hydrocarbons.

In yet one or more additional embodiments, the method further comprises purifying the N-terminal tetrapeptide fragment of etelcalcetide by recrystallization prior to coupling step (i).

In a second aspect, provided herein is a solution phase method for preparing etelcalcetide or a pharmaceutically acceptable salt thereof, comprising (i) reacting an intermediate of SEQ ID NO:5 (Compound 19) with L-cysteine in solution phase.

In one or more embodiments directed to the second aspect, the D-cysteine of Compound 19 comprises an acetamido protecting group, and the method further comprises (ii) cleaving the acetamido protecting group. In an embodiment related to the foregoing, the reacting step (i) and the cleaving step (ii) are carried out in a single reaction vessel to provide etelcalcetide.

A third aspect of the disclosure is directed to a method for preparing etelcalcetide or a precursor thereof, the method comprising: (i) coupling an acetylated N-terminal protected tripeptide fragment of etelcalcetide with a fully deprotected C-terminal tetrapeptide fragment of etelcalcetide having a free amino group in solution phase to form a protected heptapeptide fragment of etelcalcetide comprising a terminal D-cysteine. Embodiments and/or features that follow are directed to the third aspect of a method for preparing etelcalcetide or a precursor thereof.

In one or more embodiments directed to the third aspect, the acetylated N-terminal protected tripeptide fragment possessing a free C-terminal has a sequence of SEQ ID NO:9 (Ac-(D)Cys(PG)-(D)Ala-(D)Arg-OH) (Compound 36).

In yet one or more additional embodiments, the fully deprotected N-terminal tetrapeptide fragment of etelcalcetide has a sequence of SEQ ID NO:10 (H-(D)Arg-(D)Arg-(D)-Ala-(D)Arg-NH$_2$) (Compound 30).

In one or more further embodiments, the protected heptapeptide fragment of etelcalcetide has a sequence of SEQ ID NO:11 (Ac-(D)Cys(PG)-(D)Ala-(D)Arg-(D)Arg-(D)Arg-(D)-Ala-(D)Arg-NH$_2$) (Compound 37).

In yet one or more additional embodiments, the coupling is carried out in an organic solvent in the presence of a coupling reagent to provide a reaction mixture.

In one or more further embodiments, the method of the third aspect further comprises (ii) recovering the protected heptapeptide fragment of etelcalcetide from the reaction mixture.

In one or more particular embodiments related to the foregoing, the recovering step (ii) comprises adding acetonitrile to the reaction mixture to effect precipitation of the protected heptapeptide fragment of etelcalcetide.

In yet one or more additional embodiments, the method further comprises (iii) coupling in solution the terminal D-cysteine of the protected heptapeptide fragment of etelcalcetide with protected L-cysteine via formation of a disulfide bond to form etelcalcetide.

In yet one or more further embodiments, the D-cysteine of the protected heptapeptide fragment of etelcalcetide comprises a trityl protecting group, and the method further comprises (ii-a) cleaving the trityl protecting group prior to coupling with L-cysteine.

In yet one or more additional embodiments, the method further comprises (iv) purifying etelcalcetide. In a particular embodiment of the foregoing, etelcalcetide is purified by ion-exchange chromatography. In yet a further embodiment, the ion-exchange chromatography step is followed by nanofiltration, i.e., for removal of salts. In an alternative embodiment, the purifying step (iv) comprises purifying etelcalcetide by ion-exchange/nanofiltration, wherein the method may further comprise (v) lyophilizing the nanofiltered etelcalcetide.

In one or more embodiments related to the third aspect, the method further comprises, prior to the coupling step (i), (a) preparing in solution phase a C-terminal tetrapeptide fragment of etelcalcetide.

In one or more embodiments related to the foregoing, the preparing step (a) comprises:

(a-i) coupling N-protected D-alanine with H-(D)-arginamide hydrochloride in solution in the presence of a coupling agent to form N-protected D-Ala-Arg-NH$_2$ hydrochloride, (a-ii) treating the N-protected D-Ala-Arg-OH with sodium tetraphenyl borate to form a tetraphenyl borate salt, (a-iii) extracting the tetraphenylborate salt from (a-ii) into an organic solvent;

(a-iv) converting the tetraphenyl borate salt into a hydrochloride salt, (a-v) deprotecting, e.g., removing the N-protecting Cbz (Z) group from, the hydrochloride salt from (a-iv) to form a dipeptide, H-D-Ala-D-Arg-NH$_2$ hydrochloride;

(a-vi) sequentially repeating the coupling, treating, extracting and deprotecting steps on the dipeptide H-D-Ala- D-Arg-NH$_2$ hydrochloride by coupling with N-protected-D-arginine hydrochloride to form a tripeptide H-D-Arg-D-Ala-D-Arg-NH$_2$ hydrochloride, and (a-vii) sequentially repeating the coupling, treating, extracting and deprotecting steps on the tripeptide H-D-Arg-D-Ala-D-Arg-NH$_2$ hydrochloride from step (a-vi) by coupling with N-protected-D-arginine hydrochloride to form a tetrapeptide having SEQ ID NO: 12 (Compound 29), Z-D-Arg-D-Arg-D-Ala-D-Arg-N H$_2$.2 HCl.

In yet one or more additional embodiments, the method further comprises (a-viii) deprotecting the N-protected tetrapeptide fragment of SEQ ID NO:12.

Additional embodiments of the methods described herein will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description, particularly when considered in conjunction with the accompanying examples and drawings.

BRIEF DESCRIPTION OF THE FIGURES

FIG. 3 also provides an exemplary reaction scheme for coupling a protected N-terminal tetrapeptide fragment of etelcalcetide in which the N-terminus is in its free base, unprotected form, 14, with a protected tripeptide fragment of etelcalcetide, 13, in which the C-terminus is unprotected, to ultimately provide a fully protected heptapeptide precursor of etelcalcetide, 16. The heptapeptide precursor of etelcalcetide, 16, is fully protected, and corresponds to the main chain of etelcalcetide in which the D-arginines are replaced by D-ornithines. The fully protected heptapeptide fragment of etelcalcetide, 18, is produced by perguanidinylation of 17, wherein 17 has all of its ornithine δ-amino groups in unprotected (i.e., in free amino) form. See Examples 8-16.

FIGS. 8A-8L provide the structures of various compounds described herein.

DETAILED DESCRIPTION

Figure 1:
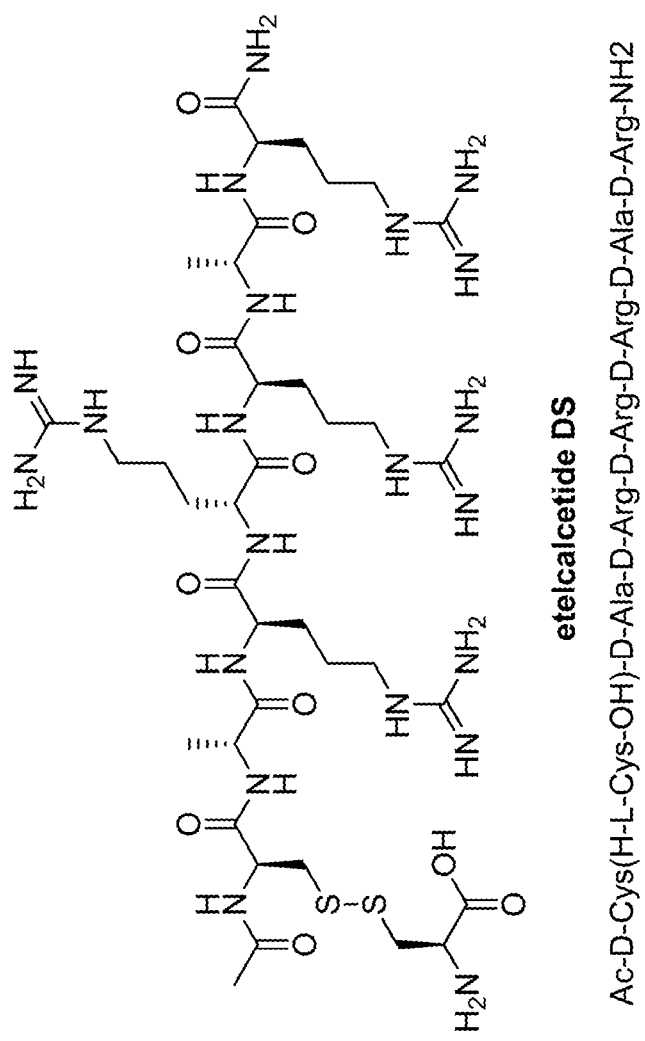
FIG. 1 provides the chemical structure of etelcalcetide (Ac-D-Cys(H-L-Cys-OH)-D-Ala-D-Arg-D-Arg-D-Arg-D-Ala-D-Arg-NH$_2$, SEQ ID NO:1).

The present disclosure now will be described more fully hereinafter. This disclosure may, however, be embodied in many different forms and should not be construed as limited to the embodiments set forth herein; rather, these embodiments are provided so that this disclosure will be thorough and complete, and will fully convey its scope to those skilled in the art.

All publications, patents and patent applications cited herein, whether supra or infra, are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, peptide, chemistry, etc., portions pertaining to such compounds, chemistry, etc. are those portions of the document which are incorporated herein by reference.

The section headings used herein are for organizational purposes only and are not to be construed as limiting the subject matter described in any way.

Definitions

It must be noted that, as used in this specification, the singular forms "a," "an," and "the" include plural referents unless the context clearly dictates otherwise.

Unless specifically noted otherwise, definitions of the terms provided herein are standard definitions used in the art, e.g., of organic synthesis, peptide synthesis, and pharmaceutical science. See, e.g., L. Otvos (Ed.), *Peptide-Based Drug Design: Methods and Protocols*, Humana Press (2010); Benoiton, L., *Chemistry of Peptide Synthesis*, CRC Press (2005); Ausubel F. M., (Ed.) et al., *Current Protocols in Molecular Biology*, John Wiley & Sons (2004). Purification techniques are typically performed according to manufacturer's specifications, as commonly conducted in the art, or as described herein. The laboratory procedures and techniques of, e.g., analytical chemistry, synthetic organic chemistry, and medicinal and pharmaceutical chemistry described herein are those that are well known and commonly used in the art.

In describing and claiming the present invention, the following terminology will be used in accordance with the definitions described below.

The term "etelcalcetide", formerly known as AMG 416, velcalcetide, and KAI-4169, refers to a compound having the chemical name: N-acetyl-D-cysteinyl-D-alanyl-D-arginyl-D-arginyl-D-arginyl-D-alanyl-D-arginamide disulfide with L-cysteine, which has the following structural formula:

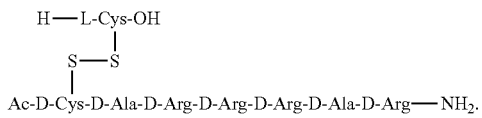

Reference to etelcalcetide, or to any compound or etelcalcetide fragment, intermediate, or precursor as described herein, is intended to encompass neutral, uncharged forms thereof, as well as pharmaceutically acceptable salts, hydrates and solvates thereof.

The terms "etelcalcetide hydrochloride" and "etelcalcetide HCl" are interchangeable and refer to a hydrochloride salt form of etelcalcetide having the following structural formula:

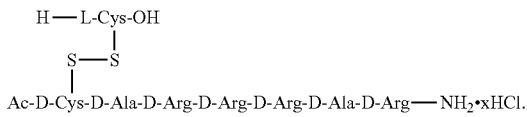

Typically, x has a value of about 4 to 5. The precise value can be determined for a given sample by chloride content analysis.

"Pharmaceutically acceptable salt" refers to a salt form of a compound having at least one group suitable for salt formation that causes no significant adverse toxicological effects to a patient. The term "pharmaceutically-acceptable salt" may, in one respect, refer to the relatively non-toxic, inorganic or organic acid addition salts of compounds as provided herein, e.g., etelcalcetide, as well as etelcalcetide fragments, intermediates, precursors, and the like, possessing one or more ionizable amine groups. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "*Pharmaceutical Salts*", *J. Pharm. Sci.* 66:1-19).

In some cases, a compound may contain one or more acidic functional groups. In such cases, the compound will form a pharmaceutically-acceptable salt with a pharmaceutically-acceptable base. The term "pharmaceutically-acceptable salts" in such an instance refers to the relatively non-toxic, inorganic and organic base addition salts of such compounds. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. Suitably pharmaceutically acceptable salt forms can be found in, e.g., *Handbook of Pharmaceutical Salts: Properties, Selection and Use*, Weinheim/Zurich:Wiley-VCH/VHCA, 2002; P. H. Stahl and C. G. Wermuth, Eds.

The phrase "protecting group" or "PG" as used herein refers to a temporary substituent or substituents that protect a potentially reactive functional group from an undesired chemical transformation. Examples of such protecting groups include esters of carboxylic acids, silyl ethers of alcohols, and acetals and ketals of aldehydes and ketones, respectively. See, e.g., Greene, T. W.; Wuts, P. G. M. *Protective Groups in Organic Synthesis*, 4th ed.; Wiley: New York, 2007; Isidro-Llobet, A., et al., *Amino Acid-Protecting Groups, Chem. Rev* 2009, 109, 2455-2504. Reactive amino acids or peptide fragments as described herein often suitably contain one or more protecting groups on functionalities that are not the target of a subject chemical transformation. Exemplary protecting groups include, e.g., carboxybenzyl, also referred to as benzyloxycarbonyl ("Cbz" or "Z"), 9-fluorenylmethoxycarbonyl (Fmoc), tert-butyloxycarbonyl (Boc), trityl (Trt), methyl ester (OMe), amide, and the like. In the shorthand structures provided herein, —NH$_2$ at the C-terminus signifies an amide protecting group (–C(O)NH$_2$), "H" at the N-terminus refers to a free amino group, and designation of a protecting group in parentheses signifies that the protecting group is on the δ nitrogen of ornithine.

A "free amino acid" or "free amino group" refers to an amino acid, peptide fragment, or peptide having an amino group that is in the form of —NH$_2$, that is, is unprotected.

As used herein, the terms "coupling agent", "condensing agent", "condensation activating agent", used interchangeably herein, refer to a chemical reagent that facilitates reaction of an amino group from one amino acid with a carboxyl group from another amino acid to form a peptide bond. Exemplary coupling agents are well-known in the art and include but are not limited to carbodiimides such as N,N'-diisopropylcarbodiimide (DIC), dicyclohexylcarbodiimide (DCC), 1-[Bis(dimethylamino)methylene]-1H-1,2,3-triazolo[4,5-b]pyridinium 3-oxide hexafluorophosphate (HATU), [benzotriazol-1-yloxy(dimethylamino)methylidene]-dimethylazanium; tetrafluoroborate (TBTU), N,N,N', N'-tetramethyl-O-(1H-benzotriazol-1-yl)uronium hexafluorophosphate, O-(benzotriazol-1-yl)-N,N,N',N'-tetramethyluronium hexafluorophosphate (HBTU), and N,N-diisopropylethyl amine (IPEA). Such compounds are readily available from commercial vendors.

The term "coupling" as used herein refers to the reaction between two amino acids, or two peptide fragments, or the reaction of an amino acid with a peptide fragment, to thereby form a peptide having a chain length that is elongated over that of the reactants. Generally, a coupling reaction results in formation of a new peptide or amide bond between two amino acids, or between an amino acid and peptide fragment, or between two peptide fragments, however, the term "coupling" as used herein may also result in the formation of a disulfide bond, for example, when reacting cysteine thiol groups to form a disulfide bridge (as in the case of introduction of L-cysteine to the main chain of etelcalcetide).

The term "treating" refers to any indicia of success in the treatment or amelioration of an injury, pathology or condition, including any objective or subjective parameter such as abatement; remission; diminishing of signs or symptoms or making the injury, pathology or condition more tolerable to the patient; slowing in the rate of degeneration or decline; making the final point of degeneration less debilitating; improving a patient's physical or mental well-being. The treatment or amelioration of signs or symptoms can be based on objective or subjective parameters, including the results of a physical examination. For example, administration of etelcalcetide can be used to treat SHPT in hemodialysis patients with CKD-MBD by decreasing serum intact parathyroid hormone (iPTH).

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with the disease state (e.g., elevated PTH levels). A "therapeutically effective amount" is an amount sufficient to remedy a disease state or symptoms, particularly a state or symptoms associated with the disease state, or otherwise prevent, hinder, retard or reverse the progression of the disease state or any other undesirable symptom associated with the disease in any way whatsoever. The full therapeutic effect does not necessarily occur by administration of one dose, and may occur only after administration of a series of doses. Thus, a therapeutically effective amount may be administered as a single dose or may be administered in multiple doses.

The terms "therapeutically effective dose" and "therapeutically effective amount," as used herein, means an amount that elicits a biological or medicinal response in a tissue system, animal, or human being, which includes alleviation or amelioration of the signs or symptoms of the disease or disorder being treated, i.e., an amount of etelcalcetide that supports an observable level of one or more desired biological or medicinal response, for example lowering PTH.

The term "peptide" refers to a compound containing two or more amino acids in which the carboxyl group of one amino acid is linked to the amino group of a another amino acid. Thus, etelcalcetide and fragments, intermediates and precursors thereof containing two or more amino acids (dipeptides, tripeptides, tetrapeptides, and so forth) are referred to herein generally as peptides. The term peptide also applies to peptides in which one or more amino acid residues is an analog or mimetic of a corresponding naturally occurring amino acid, as well as to peptides comprising only naturally occurring amino acids. A peptide as provided herein may also be modified, e.g., by the addition of carbohydrate residues to form glycoproteins, or phosphorylated.

A "variant" of a peptide comprises an amino acid sequence wherein one or more amino acid residues are inserted into, deleted from and/or substituted into the amino acid sequence relative to another polypeptide sequence. Variants include fusion proteins.

A "derivative" of a peptide is a peptide that has been chemically modified in some manner distinct from insertion, deletion, or substitution variants, e.g., via conjugation to another chemical moiety. Such modification can include, e.g., the covalent addition of a group to the amino and/or carboxy termini of the peptide or polypeptide, e.g., acetylation of the amino terminus and/or amidation of the carboxy terminus of a peptide or polypeptide. In instances in which the chemical modification is the introduction of one or more protecting groups, such peptide will generally be referred to herein as in protected form.

The term "amino acid" includes its normal meaning in the art. The twenty naturally-occurring amino acids and their abbreviations follow conventional usage. See, Immunology-A Synthesis, 2nd Edition, (E. S. Golub and D. R. Green, eds.), Sinauer Associates: Sunderland, Mass. (1991). Stereoisomers (e.g., D-amino acids) of the 19 conventional amino acids (except glycine), unnatural amino acids such as [alpha]-, [alpha]-disubstituted amino acids, N-alkyl amino acids, and other unconventional amino acids may also be suitable components for a peptide as provided herein and are included in the term, "amino acid." Examples of unconventional amino acids include: homocysteine, ornithine, 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the peptide notation used herein, the left-hand direction is the amino terminal direction and the right-hand direction is the carboxyl-terminal direction, in accordance with standard usage and convention.

Chiral purity refers to the diastereomeric purity of a peptide fragment or peptide. For example, a peptide fragment having a chiral purity of 98% means that 98% of the peptide fragment is in the form of a single diastereomer. The peptides and peptide fragments provided by the method described herein generally exhibit a chiral purity of greater than 95%, and often greater than 98%, and preferably of at least 99%.

The abbreviation "UNCA" refers to a urethane-protected amino acid N-carboxy anhydride. Illustrative UNCA compounds as provided herein include compounds 1 and 4.

The term, "room temperature" as used herein refers to a temperature falling within a range of 16° C. and 26° C.

A reaction or process that is carried out in "solution phase" is conducted in solution rather than with the use of a solid support such as employed in conventional solid phase peptide syntheses. In solid phase peptide synthesis ("SPPS"), a growing peptide chain is linked to a solid support.

A continuous solution phase process is a solution phase process as described above in which intermediates that are formed in the process are not isolated or purified but are carried on to subsequent transformation steps. Generally, a continuous solution phase process is one in which by-products and excess reagents can be removed by filtration or extraction, or are in gaseous form, to thereby allow the elimination of time-consuming isolation and purification of intermediates.

A "subject" or "patient" as used herein refers to any mammal; in a typical embodiment, the subject or patient is a human.

"Optional" or "optionally" means that the subsequently described circumstance may or may not occur, so that the description includes instances where the circumstance occurs and instances where it does not.

The term "substantially" in reference to a certain feature or entity means to a significant degree or nearly completely (i.e. to a degree of 85% or greater) in reference to the feature or entity.

The term "about", particularly in reference to a given quantity, is meant to encompass deviations of plus or minus five percent.

Additional definitions may also be found in the sections which follow.

Overview

The instant disclosure provides solution phase methods for preparing etelcalcetide, or intermediates and precursors thereof, using fragment coupling strategies.

In a first solution phase approach, the main chain of etelcalcetide is assembled by solution phase fragment coupling of two peptide fragments, where the fragments are prepared using urethane protected amino acid N-carboxy anhydride (UNCA) starting materials/reactants. Preferably, the etelcalcetide fragments are prepared using a continuous process, i.e., one that does not require intermediate isolation or purification steps. The etelcalcetide fragments employed in the first approach contain D-ornithine amino acids in place of D-arginine. The use of D-ornithine-containing fragments rather than their D-arginine counterparts allows the circumvention of undesirable side-reactions associated with the presence of guanidine. Both fragments used in the coupling strategy for assembling a precursor of etelcalcetide, i.e., one having D-ornithine residues in place of D-arginines, are surprisingly and advantageously crystallizable, meaning that the fragments can be purified by crystallization. The ability to form crystalline intermediates provides a facile and cost-effective method for providing highly pure process intermediates without having to rely on time-consuming, costly, solvent-intensive chromatographic methods. An additional advantageous feature of the first approach is the ability to carry out a global guanylation (i.e., a single reaction) on the etelcalcetide heptapeptide precursor to thereby replace the D-ornithines with D-arginine. Following assembly of the main chain of etelcalcetide and global guanylation, an L-cysteine is introduced via disulfide bond formation.

In a second solution phase fragment coupling approach utilizing a convergent synthetic strategy, an acetylated N-terminal protected tripeptide is coupled to a fully deprotected C-terminal tetrapeptide to form to form a heptapeptide etelcalcetide intermediate. In this solution phase approach, chain elongation (i.e., coupling reactions) is carried out using amino acids/peptide fragments having unprotected arginine residues. Using this methodology, arginine-containing peptide fragments such as a C-terminal tetrapeptide and its related precursor di- and tripeptides of etelcalcetide, are prepared and converted to their tetraphenyl borate salt(s), to allow simplified removal of by-products and impurities, without the need for protection of the arginine side-chains during work up. Following the removal of reaction by-products and impurities, the tetraphenyl borate salt form of an arginine-containing fragment is typically converted to an inorganic salt, e.g., a hydrochloride salt. Formation of etelcalcetide from the heptapeptide backbone is then carried out, e.g., by formation of a disulfide bridge with L-cysteine.

Features of the above methods will now be described in detail in the sections which follow.

Solution Phase Method 1

As described above, the first method for preparing etelcalcetide generally comprises the solution phase coupling of (a) a protected tetrapeptide fragment of etelcalcetide in which D-arginines have been replaced by D-ornithines with (b) a protected tripeptide fragment of etelcalcetide, to provide a protected heptapeptide precursor of etelcalcetide. The heptapeptide precursor of etelcalcetide corresponds to the main chain or backbone portion of etelcalcetide in which D-arginines have been replaced by D-ornithines. The protected heptapeptide precursor of etelcalcetide is then perguanylated to replace D-ornithines with D-arginines to provide a protected heptapeptide fragment of etelcalcetide, followed by introduction of the cysteine side chain via formation of a disulfide bond.

Figure 2:
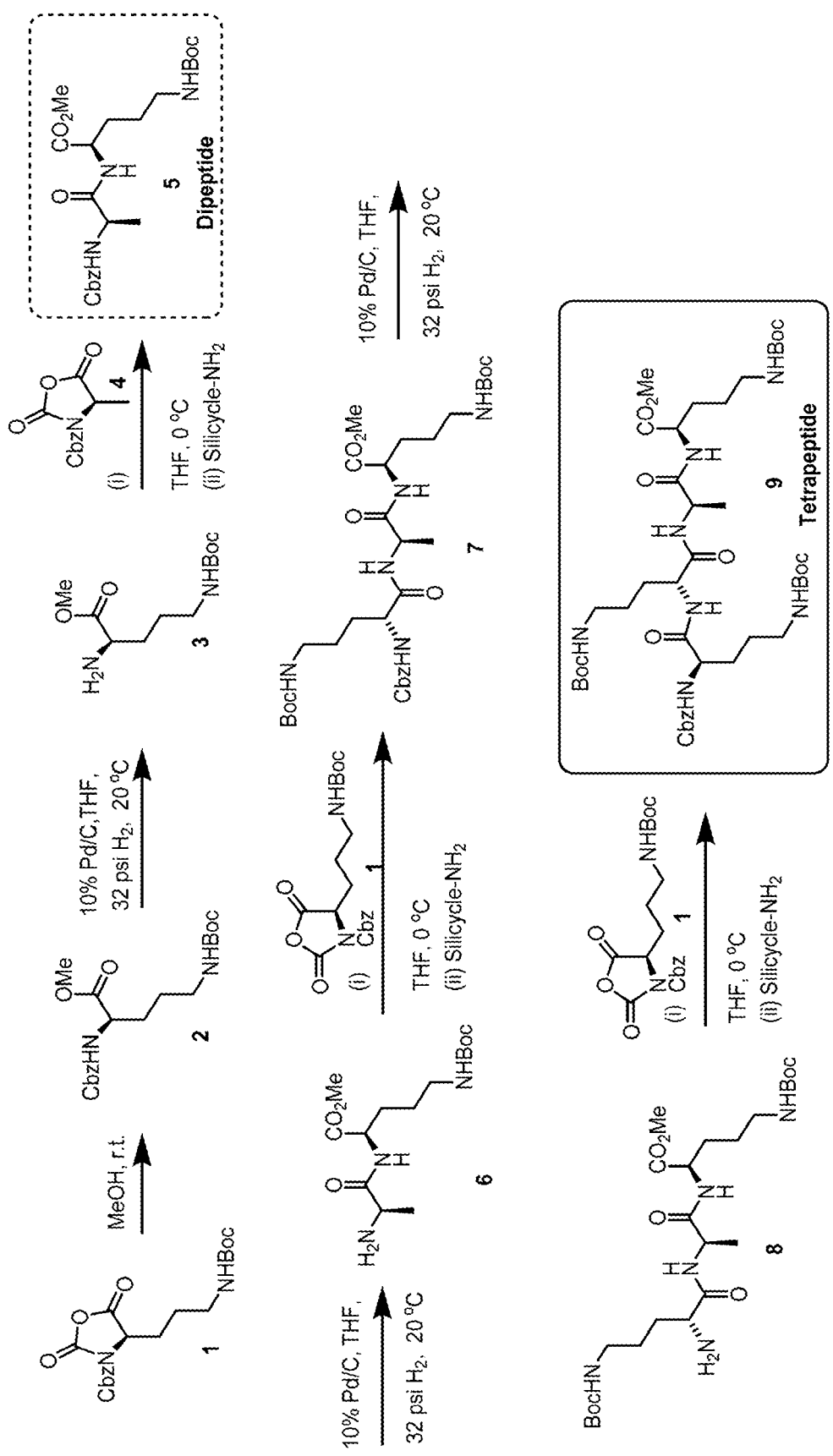
FIG. 2 provides an illustrative solution phase reaction scheme for preparing a fully protected N-terminal tetrapeptide fragment of etelcalcetide having a sequence of SEQ ID NO:13 (Compound 9, Z-D-Orn(Boc)-D-Orn(Boc)-D-Ala-Orn(Boc)-OMe). See Examples 1-7.

An exemplary solution phase reaction scheme for preparing a fully protected tetrapeptide fragment of etelcalcetide (Compound 9) is provided in FIG. 2. A "fully protected" peptide fragment is one in which all susceptible reactive functional groups in the fragment are protected. See, e.g., Compound 9. A "protected" peptide fragment or amino acid refers to a peptide or amino acid having suitable protecting groups at all susceptible reactive sites within the peptide fragment or amino acid with the exception of the functional group that is the intended target of the transformation/coupling reaction.

In reference to FIG. 2, an N-protected N-carboxyanhydride of protected D-ornithine is used to introduce D-ornithine into the growing peptide chain (in place of D-arginine) to form the tetrapeptide intermediate. The starting material, benzyloxycarbonyl (Cbz) protected N-carboxyanhydride 1, can be prepared from Boc protected D-ornithine as described in Biopolymers, 1996, 40, 183-205 and in International Patent Publication Nos. WO 2012/068187. Although particular protecting groups are described herein for protection/masking of terminal ($\alpha$) amino, side-chain amino, terminal carboxyl, cysteine and other amino acid or peptide functional groups, such protecting groups are provided for illustration purposes only, and are directed to one or more embodiments of the solution phase synthetic methodologies provided herein; other suitable protecting groups and corresponding deprotection strategies may be employed and are considered to fall within the scope of the present disclosure. For example, the UNCA may contain a Boc, Fmoc, Cbz or other suitable protecting group.

The anhydride ring is then opened under mild reaction conditions, e.g., in an alcoholic solvent under ambient conditions, e.g., at room temperature, to form the corresponding methyl ester, 2, followed by removal of the Cbz protecting group under suitable reaction conditions to afford the protected D-ornithine compound 3 (H-D-Orn(Boc)-OMe) having an unprotected $\alpha$-amino group available for coupling but having protecting groups at the C-terminus and the $\delta$-amino group of ornithine. The Cbz protecting group can be removed, e.g., by catalytic hydrogenolysis. Catalytic hydrogenolysis is typically employed during the chain elongation process to remove the Cbz group, while strong acids such as HBr in acetic acid, trifluoroacetic acid (TFA) at high temperatures, TFA-thioanisole, liquid hydrofluoric acid or boron tribromide may be employed for removal of the Cbz group in the final deprotection of the peptide. Illustrative reaction conditions are shown in FIG. 2.

Continuing in the preparation of a tetrapeptide fragment of etelcalcetide, compound 3, H-D-Orn(Boc)-OMe, is then reacted with a protected D-alanine UNCA, e.g., a Cbz-protected D-alanine UNCA, 4, typically in a polar aprotic solvent to provide a fully protected D-ornithine-D-arginine dipeptide, Z-D-Ala-D-Orn(Boc)-OMe, 5. Suitable polar aprotic organic solvents for carrying out an UNCA-addition reaction, include, for example, ethers, esters, polar aromatic hydrocarbons, and chlorinated hydrocarbons. Exemplary solvents include, for example, dimethylsulfoxide, N,N-dimethylformamide, N,N-dimethylacetamide, N-methyl-2-pyrrolidine, formamide, tetrahydrofuran, acetonitrile, and the like. An UNCA-addition reaction is typically carried out at temperatures ranging from about $-15°$ C. to about $60°$ C., or from about $-10°$ C. to about $30°$ C., or more preferably from about $-10°$ C. to about $25°$ C.

If desired, excess UNCA can be removed from the reaction mixture, for example, by reaction with a scavenger such as Silicycle®-$NH_2$, or any other suitable solid-supported amine, which can then be removed by filtration. Intermediate protected di-, tri- and tetrapeptides may, if desired, be further purified, for example, by recrystallization or by using chromatographic techniques. For example, the di-, tri-, and/or tetrapeptide (protected or fully protected) may be purified by column chromatography on silica gel using an eluent such as an alcohol-chlorinated hydrocarbon mixed solvent system, such as, e.g., 5% methanol in dichloromethane or chloroform. To prepare a fully protected tetrapeptide intermediate, PG-NH-D-Orn(NH-PG)-D-Orn(NH-PG)-D-Ala-Orn(NH-PG)-$CO_2$-PG, where "PG" signifies a protecting group, e.g., Z-D-Orn(Boc)-D-Orn(Boc)-D-Ala-Orn(Boc)-OMe, 9, a deprotection-coupling strategy using, e.g., a fully protected D-ornithine-D-alanine dipeptide such as compound 5, is iteratively repeated to provide the fully protected tetrapeptide intermediate. For example, deprotection of compound 5 is carried out to remove the carboxybenzyl protecting group at the N-terminus of D-alanine, e.g., by catalytic hydrogenolysis (e.g. using hydrogen gas in the presence of a palladium-carbon catalyst) to provide 6, followed by chain elongation by virtue of a reaction with a protected-D-ornithine UNCA such as Z-D-Orn(Boc) UNCA, to provide a fully protected tripeptide, 7. Compound 7 is crystallizable, that is, can be purified by recrystallization. Suitable recrystallization solvents or solvent systems include, e.g., acetonitrile. Deprotection is then once again carried out, this time on the chain elongated, fully protected tripeptide compound, 7, Z-D-Orn(Boc)-D-Ala-D-Orn(Boc)-OMe, to remove the carboxybenzyl protecting group, e.g., by catalytic hydrogenolysis, to form protected tripeptide compound 8, H-D-Orn(Boc)-D-Ala-D-Orn(Boc)-OMe. The free amino group of compound 8 is then reacted with a protected-D-ornithine UNCA, e.g., Z-D-Orn(Boc) UNCA, to provide a fully protected tetrapeptide, 9.

As can be seen in Example 7, the above UNCA-based iterative chain elongation approach was effective to provide compound 9 in greater than 90% yield. The terminal amino group of the fully protected tetrapeptide intermediate, 9, is then removed to form protected tetrapeptide intermediate 14, in which the N-terminus is available for coupling to the unprotected C-terminus of protected tripeptide fragment compound 13. The illustrative syntheses of compounds 2-9 is provided in Examples 1-7.

The protected and/or fully protected di-, tri- and tetrapeptides thus prepared are suitable for use in subsequent transformations without requiring laborious chromatographic purification. Peptide fragments may be isolated prior to solution phase coupling to other peptide fragments or amino acids, however, such materials may be isolated as crude materials without requiring further purification prior to a subsequent coupling/transformation reaction. Crude materials may be isolated, e.g., by removal of solid by-products and/or unreacted starting materials by filtration, followed by concentration of the filtrate under reduced pressure to remove solvent. See, e.g., the recovery of compounds 6 and 8. Intermediate fragments may alternatively be recovered by extraction into a suitable solvent, followed by concentration under reduced pressure.

As shown in the Examples, following removal of the α-amino protecting groups, compounds 6 and 8 were carried on to the next UNCA-amino acid chain elongation reaction without further purification of the crude product. If desired, however, the fragments may be further purified as described above, for example, by column chromatography or by recrystallization. See, e.g., Example 7, which describes purification of Compound 9, Z-D-Orn(Boc)-D-Orn(Boc)-D-Ala-Orn(Boc)-OMe (9), a fully protected tetrapeptide precursor of etelcalcetide, by recrystallization from acetonitrile. The chiral purity of the tetrapeptide fragment is typically quite high. Generally, the chiral purity is greater than 90%, or greater than 92%, or preferably greater than 95%, or even more preferably greater than 98%. As can be seen from Example 7, using the above approach, the fully protected tetrapeptide compound, 9, was prepared in 99% chiral purity.

Use of an UNCA-based strategy for forming the fully protected or protected tetrapeptide precursor compounds 9 or 14, is particularly advantageous due to the formation of a gaseous reaction product, carbon dioxide, which alleviates the need for numerous solids processing and/or removal steps.

To form a heptapeptide precursor of etelcalcetide, tetrapeptide fragment 9, following removal of the Cbz group from the N-terminal to provide tetrapeptide fragment 14, is coupled with a protected tripeptide fragment comprising a terminal D-cysteine. See, e.g., FIG. 3, which provides an exemplary reaction scheme for coupling a protected N-terminal tetrapeptide fragment of etelcalcetide having a free N-terminal amino group, 14, with a protected tripeptide fragment of etelcalcetide, 13, having its C-terminus unprotected, to ultimately provide a fully protected heptapeptide precursor of etelcalcetide, 16. The heptapeptide precursor of etelcalcetide, 16, is fully protected, and corresponds to the main chain of etelcalcetide, but comprising therein D-ornithines in place of D-arginines. The fully protected heptapeptide fragment of etelcalcetide, 18, is produced by perguanylation of 17, compound 17 having all of its ornithine δ-amino groups in unprotected (i.e., in free amino) form.

Figure 3:
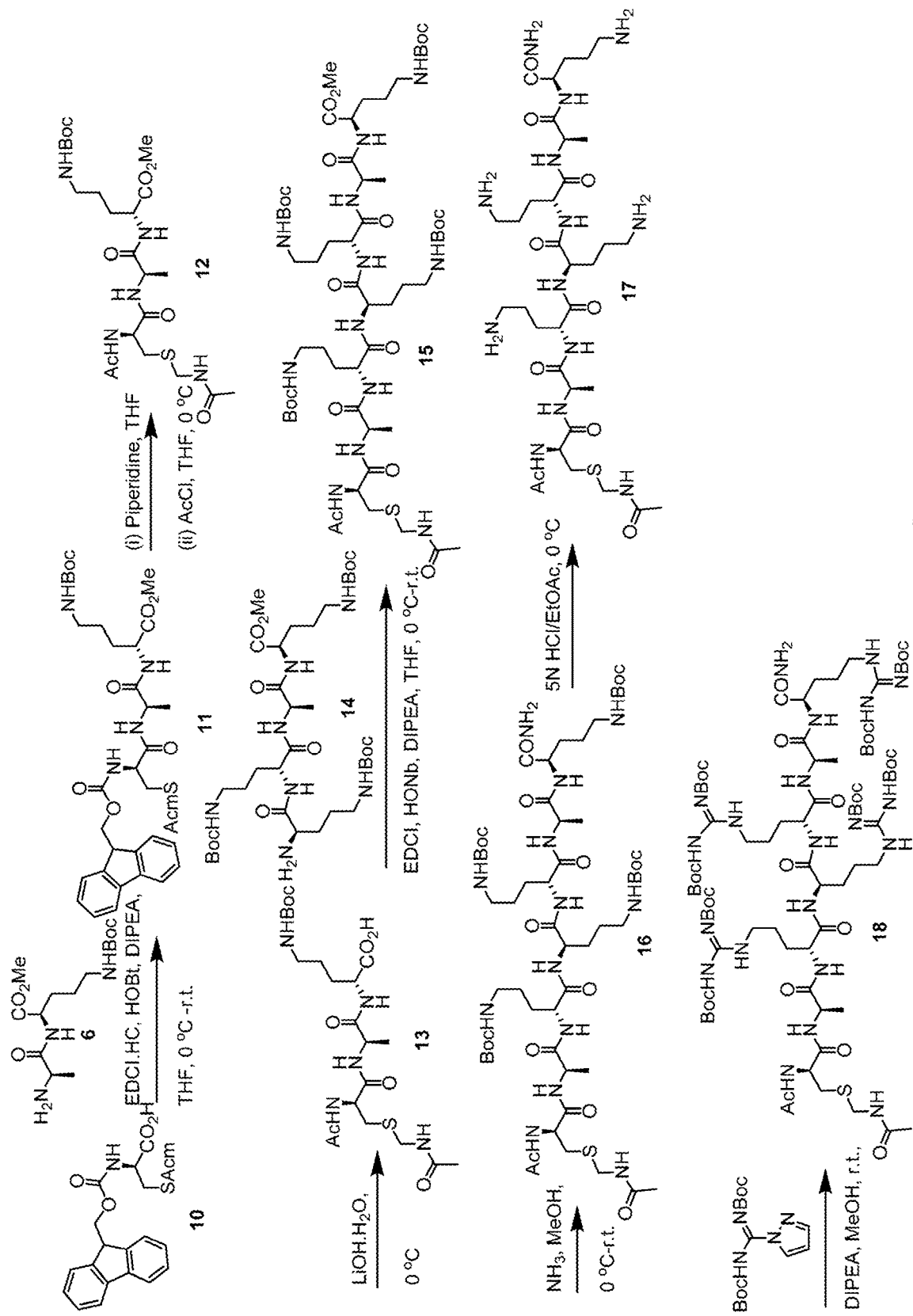
FIG. 3 provides an illustrative solution phase reaction scheme for preparing a protected tripeptide fragment of etelcalcetide having a sequence of SEQ ID NO:3 (Compound 13, Ac-D-Cys(Acm)-D-Ala-D-Orn(Boc)-OH).

Still in reference to FIG. 3, a protected tripeptide fragment of etelcalcetide, 13, having a terminal D-cysteine, is formed by coupling protected D-Cys-OH, 10, i.e., —NH-D-Cys(S-PG)OH, with an intermediate protected dipeptide fragment, H-D-Ala-D-Orn(NH-PG)-CO-PG (6), to provide a fully protected tripeptide fragment of etelcalcetide. Any suitable protecting group may be used to protect the D-cysteine thiol; suitable protecting groups include acetamidomethyl (Acm), trityl (Trt), benzyl (Bn) and methylbenzyl (Meb), tertiary butyl (tBu), p-methoxybenzyl (Mob), monomethoxytrityl (Mmt), 2-pyridine-sulfenyl (S-Pry), and tert-butylmercapto (S-tBu) with the Acm group being preferred. Specifically, in one embodiment of the method, dipeptide intermediate 6 is coupled to the commercially available amino acid 10, Fmoc-D-Cys(Acm)OH, under standard peptide coupling conditions to afford a fully protected tripeptide intermediate 11, Fmoc-D-Cys(Acm)-D-Ala-D-Orn(Boc)-OMe, or more generally, PG-NH-D-Cys(S-PG)-D-Ala-D-Orn(NH-PG)-COPG. Conventional solution phase coupling reagents that may be employed in this and other conventional coupling reactions include, for example, 6-chloro-1-hydroxybenzotriazole, N, N'-diisopropylcarbodiimide (DIC), dicyclohexylcarbodiimide (DCC), 1-[Bis(dimethylamino)methylene]-1H-1,2,3-triazolo[4,5-b]pyridinium 3-oxide hexafluorophosphate (HATU), [benzotriazol-1-yloxy(dimethylamino)methylidene]-dimethylazanium; tetrafluoroborate (TBTU), N,N,N',N'-tetramethyl-O-(1H-benzotriazol-1-yl)uronium hexafluorophosphate, O-(benzotriazol-1-yl)-N,N,N',N'-tetramethyluronium hexafluorophosphate (HBTU), and N,N-diisopropylethyl amine (IPEA); activated esters such as hydroxysuccinimidyl or p-nitrophenol esters may also be used.

The fully protected tripeptide, 11, is then deprotected, e.g., to remove the Fmoc deprotecting group, under suitable deprotecting conditions. The Fmoc protecting group can be suitably removed, e.g., by treatment with base, typically a secondary amine such as piperidine. Solution phase removal can be carried out, for example, by treatment with a base such as liquid ammonia, morpholine, piperidine, diethylamine, dimethylacetamide, or piperazine, in an organic solvent. The resulting free amino group is then protected with a different protecting group, e.g., an acetyl group, to provide fully protected compound 12, Ac-D-Cys(Acm)-D-Ala-D-Orn(Boc)-OMe, wherein the newly introduced acetyl group is stable to the reaction conditions which follow. The N-protected methyl ester compound 12 is then hydrolyzed under basic conditions to afford the protected, free acid-containing tripeptide intermediate 13, Ac-D-Cys(Acm)-D-Ala-D-Orn(Boc)-OH, which, as described previously, is coupled to the free amino tetrapeptide fragment derived from 9, compound 14, H-D-Orn(Boc)-D-Orn(Boc)-D-Ala-D-Orn(Boc)-OMe, to afford the fully protected heptapeptide intermediate 15, Ac-D-Cys(Acm)-D-Ala-D-Orn(Boc)-D-Orn(Boc)-D-Orn(Boc)-D-Ala-Orn(Boc)-OMe. The carboxylic acid methyl ester functionality in 15 is transformed to an amide group, —C(O)NH$_2$, by treatment with ammonia, to provide fully protected heptapeptide compound, 16, Ac-D-Cys(Acm)-D-Ala-D-Orn(Boc)-D-Orn(Boc)-D-Orn(Boc)-D-Ala-Orn (Boc)-NH$_2$ Compound 16 is then taken to a global deprotection step to remove all of the protecting groups, e.g, Boc or other suitable protecting groups, from the ornithine δ-amino groups, to thereby provide a compound such as 17, Ac-D-Cys(Acm)-D-Ala-D-Orn-D-Orn-D-Orn-D-Ala-Orn-NH$_2$, comprising free δ-amino groups on each of the four ornithines. A resulting heptapeptide etelcalcetide precursor such as 17 is then perguanylated, to replace the four deprotected ornithines therein with protected D-arginines. The reaction is carried out using, e.g., a pyrazole carboxamidine reagent under suitable reaction conditions to provide the fully protected etelcalcetide backbone, compound 18, Ac-D-Cyst(Acm)-D-Ala-D-Arg(Boc)$_2$-D-Arg(Boc)$_2$-D-Arg (Boc)$_2$-D-Ala-D-Arg(Boc)$_2$-NH$_2$. Exemplary guanylation reagents include, e.g., 1H-1,2,4-triazole-1-carboxamidine hydrochloride, 1-H-pyrazole-1-carboxamidine hydrochloride, and 3,5-dimethyl-1-H-pyrazole-1-carboxamidine hydrochloride. Thiourea or isothiourea-based reagents can also be used.

Figure 4:
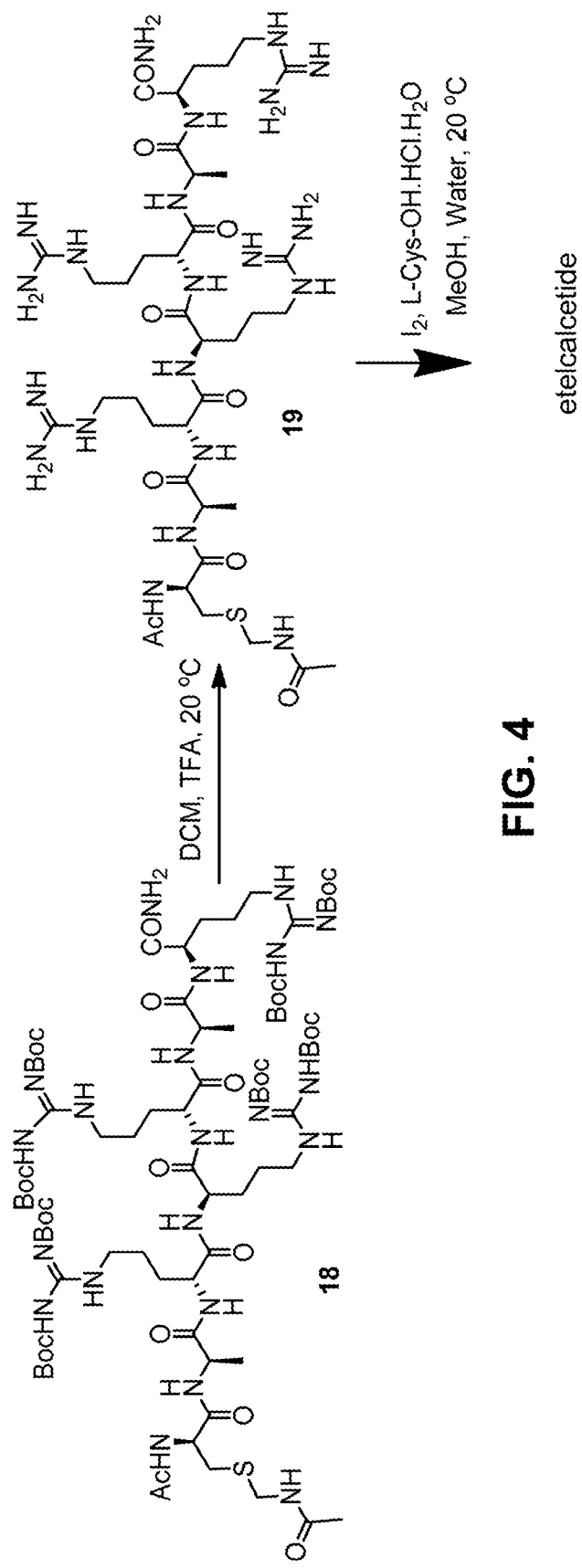
FIG. 4 illustrates global deprotection of Boc-protected arginines contained in a heptapeptide intermediate of etelcalcetide, followed by deprotection of D-cysteine, and coupling to L-cysteine to form the desired product, etelcalcetide. See Examples 15 and 16.

The D-arginine protecting groups are then globally removed from the fully protected etelcalcetide backbone. For example, as illustrated in FIG. 4, global Boc deprotection is carried out on intermediate 18, using e.g., TFA or any other suitable deprotection strategy, to provide intermediate compound 19. Intermediate compound 19 possesses a protected cysteine thiol group which is removed prior to coupling to L-cysteine to provide the desired product, etelcalcetide. As shown in exemplary FIG. 4, the acetamido protecting group in 19 can be removed by oxidative cleavage, e.g., in the presence of an oxidizing agent such as iodine, to form the free thiol, followed by coupling to L-Cys via disulfide bond formation. Additional reagents that may be used to remove the acetamido group include, e.g., thallium trifluoroacetate TI(TFA)$_3$, and mercury(II) salts such as mercury (II) acetate. Both removal of the protecting group from D-cysteine and the final coupling step in which the L-cysteine side chain is coupled to the free-thiol containing etelcalcetide backbone may be carried out in the same reaction vessel to provide the desired peptide product, etelcalcetide, 20. FIG. 4 provides exemplary reaction conditions for conducting global deprotection of Boc-protected arginines contained in the heptapeptide intermediate, followed by thiol deprotection and coupling to L-cysteine to form the desired product.

Solution Phase Method 2

Figure 7:
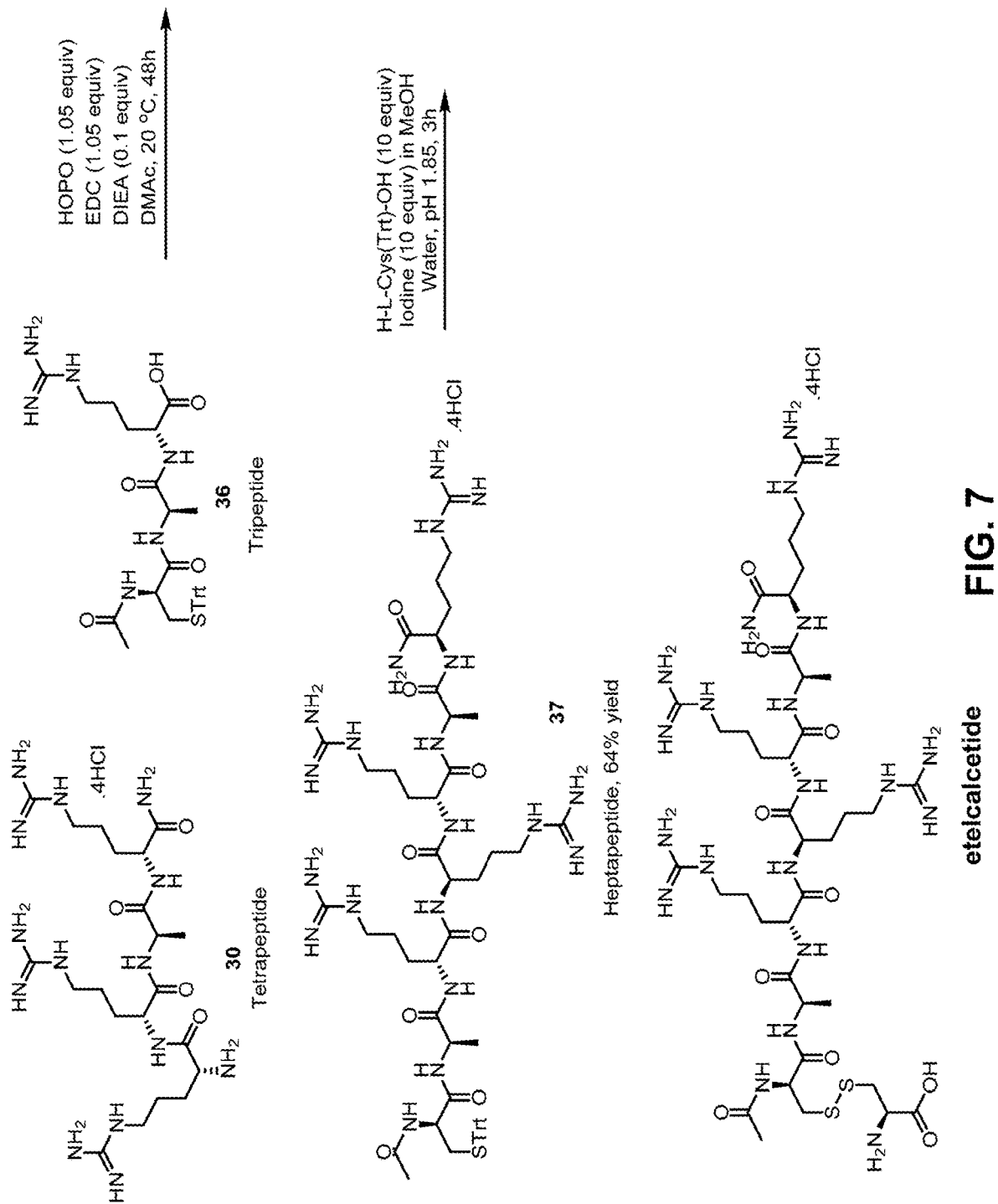
FIG. 7 provides an exemplary solution phase synthetic methodology for forming a heptapeptide of etelcalcetide. In the method, an acetylated N-terminal protected tripeptide is coupled to a fully amino deprotected C-terminal tetrapeptide to form a heptapeptide etelcalcetide intermediate. Details of the synthesis are provided in Examples 25 and 26.
Figure 8L:
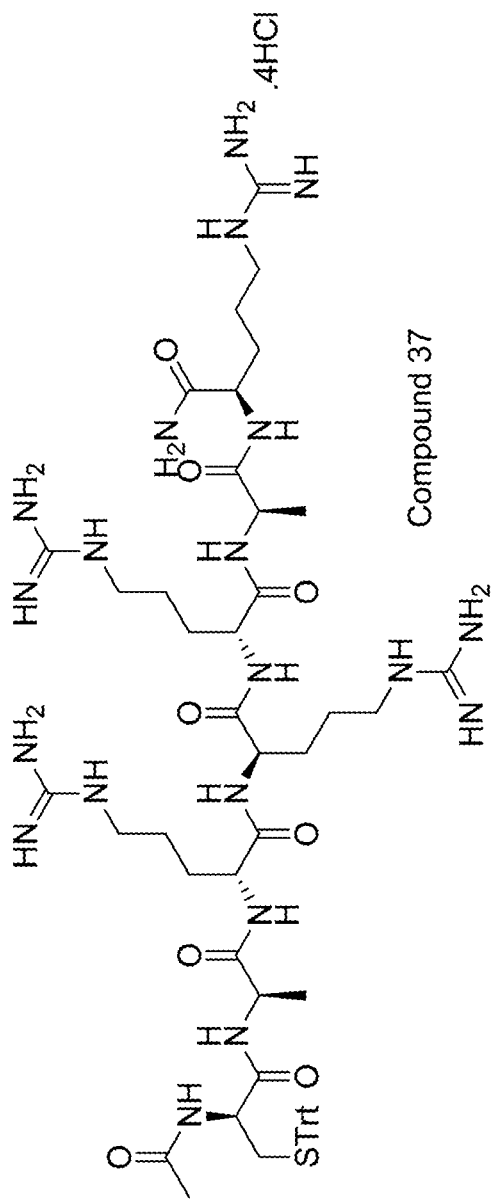

In a second aspect, provided herein is a solution phase fragment coupling method in which an acetylated N-terminal protected tripeptide having a free carboxyl group is coupled to a tetrapeptide amide comprising an unprotected arginine side chain having a free α amino group to form a heptapeptide etelcalcetide intermediate as shown schematically in FIG. 7. Using this approach, chain elongation is carried out using amino acids/peptide fragments having unprotected arginine residues. Arginine-containing peptide fragments such as a C-terminal tetrapeptide of etelcalcetide and its related precursor di- and tripeptides of etelcalcetide, are prepared and converted to their tetraphenyl borate salt(s), to allow simplified removal of by-products and impurities following a coupling reaction, without the need for protection of the arginine side-chains, e.g., during work up of the resulting reaction mixtures. Following the removal of reaction by-products and impurities, e.g., by extraction into an aqueous phase, the tetraphenyl borate salt of an arginine-containing fragment, e.g., in an organic solvent, is converted to an inorganic salt, e.g., a hydrochloride salt. Formation of etelcalcetide from the heptapeptide backbone is then carried out, e.g., by formation of a disulfide bridge with L-cysteine.

Figure 5:
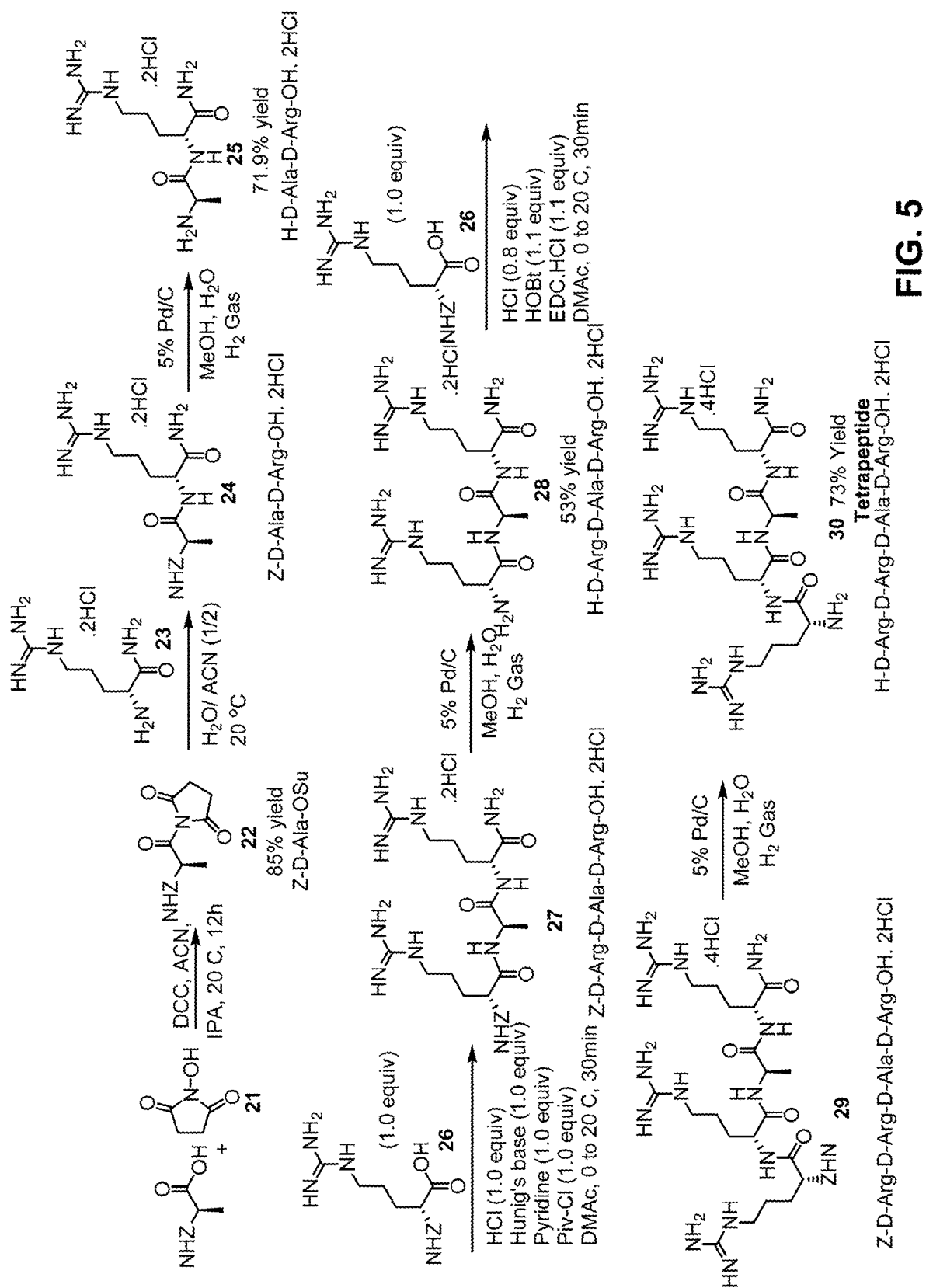
FIG. 5 illustrates an exemplary solution phase synthesis of a fully amino-deprotected C-terminal tetrapeptide fragment of etelcalcetide, Compound 30 (SEQ ID NO:10), useful for the solution phase preparation of a protected heptapeptide fragment of etelcalcetide. Details of the synthesis are provided in Examples 17-20.

Pertaining to the second solution phase synthetic methodology provided herein is a method for preparing one of the reactants using in the fragment coupling approach, i.e., a fully amino deprotected C-terminal tetrapeptide fragment of etelcalcetide. Turning now to FIG. 5, this figure demonstrates an embodiment of a method for forming a fully amino-deprotected tetrapeptide fragment 30, SEQ ID NO:10, H-(D)Arg-(D)Arg-(D)Ala-(D)Arg-NH$_2$.4HCl. The embodiment illustrated in FIG. 5 is described in Examples 17-20.

The synthesis of a tetrapeptide such as 30 may be carried out as follows. For example, amino-protected alanine having its carboxy group suitably activated, e.g., in the form of an activated ester, e.g., Z-D-Ala-OSu, 22, is coupled to arginine having its carboxyl group suitably protected as, e.g., D-arginamide hydrochloride, 23, under coupling conditions to provide a protected dipeptide fragment, PG-NH-(D)-Ala-(D)-Arg-CO-PG. The coupling reaction is carried out, for example, in an aprotic organic solvent such as, for example, dimethylacetamide, N,N-dimethylformamide (DMF), N-methylpyrrolidone (NMP), or acetonitrile, in the presence of a coupling agent such as N,N-diisopropylethyl amine, HATU or HBTU, or the like, which act as proton scavengers during the coupling reaction. The coupling reaction is typically carried out under mild conditions, e.g., at a temperature ranging from about 10° C. to about 60° C., or from about 15° C. to about 45° C., or from about 20° C. to 30° C. An exemplary D-Ala-D-Arg dipeptide comprises a terminal carboxybenzyl protected alanine amino group and the D-arginine carboxyl group protected as the corresponding amide, e.g., Z-(D)Ala-(D)Arg-NH$_2$ 24. Following coupling, water may be added to the reaction mixture, e.g., to dissolve the dipeptide, and unreacted starting materials and by-products may optionally be removed in one or more wash steps, using for example, a suitable organic solvent such as ethyl acetate. The dipeptide is then treated with sodium tetraphenylborate (TPB) to form the corresponding TPB salt. Formation of the TPB salt allows the fragment to be extracted into an organic solvent such as dichloromethane, chloroform, or any other suitable solvent. See, e.g., U.S. Patent Publication No. US20110098446. The resulting organic layer is then preferably washed one or multiple times with water to remove coupling reaction by-products and the like. Following treatment of the organic layer to remove unwanted impurities, an ion exchange reaction is carried out in a suitable solvent such as methanol, e.g., using an ion exchange column to provide the dipeptide fragment as an inorganic acid salt, e.g., as a hydrochloride salt. Removal of the terminal D-alanine amino protecting group is then carried out. For example, the carboxybenzyl group in Z-(D)Ala-(D)Arg-NH$_2$ 24 may be removed by catalytic hydrogenolysis as previously described. Details of reaction conditions suitable for carrying out the above-described coupling reaction and salt exchange are provided in Example 18. This process of coupling, tetraphenyl borate salt formation, salt exchange and deprotection is then iteratively carried out as shown in FIG. 5. For example, the coupling/hydrogenation steps are iteratively performed on 25 using PG-NH-D-arginine hydrochloride, e.g., Z-D-Arg-OH 26 to afford tripeptide 27 and subsequently the desired tetrapeptide 30 in high yield. See, e.g., Examples 19 and 20. Suitable coupling conditions can be readily determined by those skilled in the art of peptide synthesis, organic synthesis, or the like. For example, the carboxy group of an amino acid such as 26 can be activated with any suitable activating group, and the coupling reaction carried out using any of a number of coupling agents known to those of skill in the art. The particular coupling conditions shown in FIG. 5 and described in the corresponding examples are meant to be merely exemplary and are not intended to be limiting in scope. The foregoing methodology is useful for preparing a fully amino deprotected tetrapeptide such as compound 30, which is then used in a solution phase coupling reaction to form a protected heptapeptide fragment of etelcalcetide. The number of acid molecules contained in an acid addition salt, such as an HCl salt, can vary since different ion-exchanged products will have different capacities to retain an acid, e.g., HCl. In preparing etelcalcetide, additional basic sites available to form an HCl salt are introduced into the growing peptide chain as additional arginines are introduced.

Figure 6:
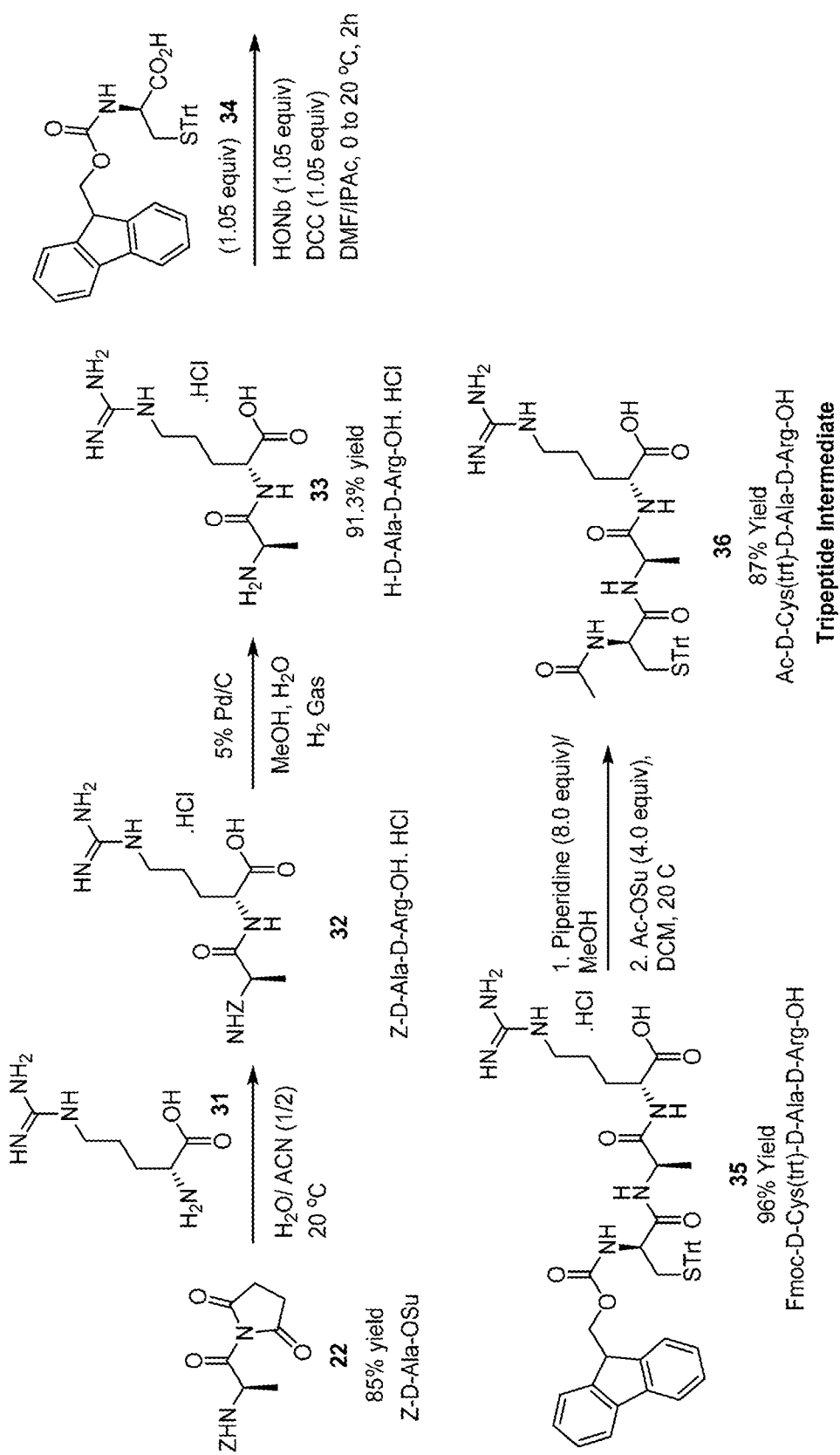
FIG. 6 provides an exemplary solution phase synthetic methodology for preparing an acetylated N-terminal protected tripeptide fragment of etelcalcetide, Compound 36 (SEQ ID NO:9), useful for the solution phase preparation of a protected heptapeptide fragment of etelcalcetide. Details of the synthesis are provided in Examples 21-24.

FIG. 6 provides an exemplary reaction scheme and exemplary reaction conditions for preparing an acetylated N-terminal protected tripeptide fragment of etelcalcetide. The tripeptide fragment containing a D-cysteine amino acid for coupling with the above-described tetrapeptide may be assembled in a similar manner as described above for the tetrapeptide, with the exception that the starting material is H-D-Arg-OH, 31. Unprotected alanine, H-D-Arg-OH, 31, is coupled to amino-protected alanine having its carboxy group suitably activated, e.g., in the form of an activated ester, e.g., Z-D-Ala-OSu, 22, under coupling conditions suitable to provide a protected dipeptide fragment, PG-NH-(D)-Ala-(D)-Arg-OH. When the resulting dipeptide is carboxybenzyl-protected, the dipeptide corresponds to 32, Z-D-Ala-(D)-Arg-OH HCl. Deprotection of the dipeptide is then carried out, using deprotection conditions appropriate for the particular protecting group employed. For example, dipeptide 32 may be subjected to hydrogenolysis to thereby remove the Z protecting group. The resulting fully deprotected dipeptide is H-D-Ala-D-Arg-OH, 33. The tripeptide is then formed, e.g., by coupling the free amino group in 33 with PG-NH-D-Cys(SH-PG)-OH, i.e., an N-terminal protected, thiol-protected cysteine such as Fmoc-D-Cys(trt)-OH, 34 to form a protected tripeptide, 35, Fmoc-D-Cys(trt)-D-Ala-D-Arg-OH. The coupling reaction is carried out under coupling conditions well-known in the art. As described, coupling can, for example, be carried out using a carbodiimide coupling agent. In particular, the coupling reaction may be effected using the activators hydroxynorbornene/DCC in a suitable solvent system, e.g., a dimethylformamide-isopropyl alcohol solvent mixture, to provide the desired tripeptide. The resulting tripeptide is then deprotected, i.e., the N-terminal protecting group is removed using a suitable deprotection methodology. For example, the Fmoc group is removed by treatment with base in an organic solvent. For example, the Fmoc protecting group is removed from 35 by treatment with a molar excess of piperidine in methanol, and the free amino group in the resulting tripeptide is then capped with an acetyl group to provide an acetylated N-terminal protected tripeptide fragment of etelcalcetide, e.g., 36.

The intermediate compounds, i.e., the acetylated N-terminal protected tripeptide fragment and the fully amino deprotected C-terminal tetrapeptide fragment of etelcalcetide, are then coupled to form a protected heptapeptide fragment of etelcalcetide comprising a terminal D-cysteine. See, e.g., Example 25. As described therein, H-(D)Arg-(D)Arg-(D)Ala-(D)Arg-NH$_2$.4HCl, 30, or a suitably protected equivalent thereof, is coupled with Ac-D-Cys(Trt)-D-Ala-D-Arg-OH, 36, or a suitably protected equivalent thereof, in solution to provide a protected heptapeptide fragment of etelcalcetide such as 37. Coupling of the tri- and tetrapeptide fragments is carried out using one or more coupling agents and coupling conditions as well known in the art. For example, the fragments may be coupled using a carbodiimide coupling agent, or a phosphonium or aminium salt. For example, the coupling reaction may be carried out using a carbodiimide coupling agent, optionally in the presence of a hydroxylamine derivative, such as N-hydroxysuccinimide (HOSu), HODhbt, HOBt, HOAt, or a 1-hydroxy-1,2,3-triazole derivative. Illustrative coupling conditions include the use of a carbodiimide coupling reagent such as EDC, in the presence of 2-hydroxypyridine-N-oxide. Diisopropylethylamine can also be added to the reaction mixture, e.g., to accelerate the rate of reaction. Additional reagents and coupling conditions suitable for use in the coupling reactions described herein may be found, e.g., in "Recent development in peptide coupling reagents", Al-Warhi, T. I., et al., *J. of Saudi Chemical Society* (2012), 16, 97-116. The coupling reaction is generally carried out at temperatures ranging from about −25° C. to about 60° C., or from about 0° C. to about 40° C., or from about 0° C. to about 25° C., depending upon the coupling agent employed. The coupling reaction is generally carried out in an aprotic solvent such as dimethylacetamide. Aprotic solvents suitable for use in coupling reactions are described previously herein. Upon completion of the coupling reaction, the crude heptapeptide can be recovered from the reaction mixture, e.g., by precipitation with acetonitrile. If desired, the heptapeptide fragment can be further purified using any suitable peptide purification method known in the art. In one embodiment, the heptapeptide is purified by chromatography.

The cysteine side chain is then introduced to a protected heptapeptide fragment of etelcalcetide such as 37, i.e., comprising in protected form the main chain of etelcalcetide having a terminal D-cysteine, by reaction of the cysteine thiol groups under oxidizing conditions to form a disulfide bridge. For example, disulfide bond formation can be carried out by reacting the protected heptapeptide fragment of etelcalcetide with an excess of thiol-protected L-cysteine, e.g., H-L-Cys(Trt)-OH, in the presence of iodine. Generally, an excess of iodine is used, and the reaction may be carried out, for example in water or in a water-containing solvent. The reaction is typically carried out at a pH from about 2 to about 7.5. In one embodiment, the thiol-coupling reaction is carried out at a pH of less than 7, e.g., from about 2 to about 5. Lowering the pH of the reaction solution can, for example, aid in dissolution of the protected cysteine reactant, L-H-Cys(trt)-OH. This final L-cysteine coupling reaction is carried out, for example, in a manner similar to that described under solution phase method 1 to provide the desired product, etelcalcetide. The use of iodine to facilitate disulfide bond formation conveniently allows oxidative cleavage of both the acetamido group and the trityl group to provide the desired product. The product obtained in solution-phase, etelcalcetide, is typically further purified. Reaction by-products are removed from the reaction mixture, for example by extraction with a suitable solvent, and the crude product is purified using conventional separation and/or purification techniques. For instance, in one embodiment, crude etelcalcetide is purified by ion-exchange chromatography. Salts present in the collected fractions after ion-exchange treatment may, for example, be removed by nanofiltration.

EXAMPLES

The following examples are intended to be purely exemplary and are in no way intended to limit the scope of the appended claims. There are numerous variations and combinations of reaction conditions, e. g., component concentrations, solvents, solvent mixtures, temperatures, protecting groups, and other reaction parameters and conditions that may be employed to optimize product characteristics such as purity, yield, and the like. Such are considered as well within the scope of the present disclosure.

Example 1

Synthesis of (R)-Methyl 2-(benzyloxycarbonylamino)-5-(tert-butoxycarbonylamino)pentanoate, Compound 2

Z-D-Orn(Boc)-OMe (2).

A solution of Z-D-Orn(Boc) UNCA (1); 60 g, 157.7 mmol) in anhydrous MeOH (1000 mL) at ambient temperature under nitrogen atmosphere was stirred for 0.5 h, by which time reaction was completed as indicated by TLC. Excess solvent was removed under reduced pressure to generate 2 (55.0 g, 95%) as a thick gum. The material was used in the next step without further purification. $^1$H NMR (300 MHz, DMSO-$d_6$). δ 7.71 (d, J=7.5 Hz, 1H), 7.32 (m, 5H), 6.77 (bs, 1H), 5.01 (s, 2H), 3.99 (m, 1H), 3.60 (s, 3H), 2.87 (dd, J=12.1, 6.1 Hz, 2H), 1.63 (m, 2H), 1.54 (m, 2H), 1.39 (s, 9H); $^{13}$C NMR (75 MHz, DMSo-$d_6$). δ 173.3, 156.6, 156.0, 137.9, 128.8, 128.3, 128.2, 127.6, 77.8, 65.9, 54.1, 52.2, 28.7, 28.5, 26.4; MS ESI (m/z) calcd. for $C_{19}H_{29}N_2O_6$ [M+H-Boc]$^+$ 281, found 281; HPLC purity. 99.5%; Chiral purity. 100%.

Example 2

Synthesis of (R)-Methyl 2-amino-5-(tert-butoxycarbonylamino)pentanoate, Compound 3

H-D-Orn(Boc)-OMe (3).

Into a solution of 2 (15.0 g, 39.4 mmol) in anhydrous EtOAc (250 mL) were added Pd—C (2 g, 10% on activated charcoal) under a nitrogen atmosphere, and a catalytic amount of acetic acid, and the resulting solution was stirred for 16 h at ambient temperature under hydrogen pressure (3 kg). Completion of the reaction was indicated by TLC (dipped in ninhydrin solution, dried and heating). The reaction mixture was passed through a pad of Celite; solid on the filter was washed with EtOAc (100 mL). The filtrate thus obtained was concentrated under reduced pressure to obtain a crude residue. The crude mass was co-evaporated twice with toluene to afford 3 (11.2 g; crude) as a thick gum, which was used without further purification.

Example 3

Synthesis of (5R,8R)-Methyl 5,15,15-trimethyl-3,6,13-trioxo-1-phenyl-2,14-dioxa-4,7,12-triazahexadecane-8-carboxylate, Compound 5

Z-D-Ala-D-Orn(Boc)-OMe (5).

To a well-stirred solution of 3 (11.0 g crude) in anhydrous THF (250 mL) under nitrogen atmosphere was added (R)-benzyl 4-methyl-2,5-dioxooxazolidine-3-carboxylate, 4 (11.2 g, 47.3 mmol) at 0° C. and the contents were stirred for 2 h at ambient temperature, after which reaction was completed as indicated by TLC. To the flask, silicycle amine (5 g) was added, and stirring was continued at ambient temperature for another 16 h to strip off the residual anhydride. Silicycle amine was filtered off and the filtrate was evaporated under reduced pressure to have a crude residue. Purification of the crude mass by silica-gel (230-400 mesh) flash column with 2% MeOH/CHCl$_3$ produced 5 (12.0 g, 67%) as a white solid. $^1$H NMR (300 MHz, DMSO-$d_6$). δ 8.18 (d, J=7.3 Hz, 1H), 7.35 (m, 6H), 6.77 (bs, 1H), 4.99 (s, 2H), 4.12 (m, 2H), 3.59 (s, 3H), 2.87 (m, 2H), 1.61 (m, 2H), 1.36 (m, 2H), 1.35 (s, 9H), 1.18 (d, J=7.1 Hz, 3H); $^{13}$C NMR (100 MHz, DMSO-$d_6$). δ 173.2, 172.9, 156.0, 137.5, 128.8, 128.2, 128.19, 77.9, 65.8, 52.2, 50.2, 28.7, 28.6, 26.4, 18.6; MS ESI (m/z) $C_{22}H_{34}N_3O_7$ [M+H-Boc]$^+$ 352, found 352; HPLC purity. 99.9%.

Example 4

Synthesis of (R)-Methyl 2-((R)-2-aminopropanamido)-5-(tert-butoxycarbonylamino)pentanoate, Compound 6, SEQ ID NO:6

H-D-Ala-D-Orn(Boc)-OMe (6).

Into a solution of 5 (56.0 g, 124.1 mmol) in anhydrous THF (500 mL) was added Pd—C (6 g, 10% on activated charcoal; wet basis) under nitrogen atmosphere, and the resulting solution was agitated for 2 h at ambient temperature under hydrogen pressure (40 psi). Completion of the reaction was indicated by TLC (dipped in ninhydrin solution, dried and heating). The reaction mixture was passed through a pad of Celite, solid on the filter was washed with THF (200 mL), filtrate thus obtained was concentrated under reduced pressure to furnish 6 (38.0 g; crude) as a black tar, which was used without further purification.

Example 5

Synthesis of (9R,12R,15R)-Methyl15-(benzyloxycarbonylamino)-2,2,12,22,22-pentamethyl-4,11,14,20-tetraoxo-3,21-dioxa-5,10,13,19-tetraazatricosane-9-carboxylate, Compound 7, SEQ ID NO:7

Z-D-Orn(Boc)-D-Ala-D-Orn(Boc)-OMe (7).

To a well-stirred solution of 6 (38.0 g; crude) in anhydrous THF (500 mL) was added 1 (51.7 g, 131.8 mmol) at 0° C. under nitrogen atmosphere and the contents were stirred for 2 h at ambient temperature after which reaction was completed as indicated by TLC. To the flask, silicycle amine (15 g) was added, and stirring was continued at ambient temperature for another 16 h to strip off the residual anhydride. Silicycle amine was filtered off and the filtrate was evaporated under reduced pressure to have a crude residue. The crude mass was re-crystallized from acetonitrile (6 volumes) to produce 7 (45.0 g, 55%) as a white solid. $^1$H NMR (300 MHz, DMSO-$d_6$). δ 8.19 (d, J=7.2 Hz, 1H), 7.92 (d, J=7.6 Hz, 1H), 7.36 (m, 6H), 6.76 (m, 2H), 4.99 (s, 2H), 4.29 (m, 1H), 4.18 (m, 1H), 3.94 (m, 1H), 3.58 (s, 3H), 2.87 (m, 4H), 1.58 (m, 8H), 1.35 (m, 18H), 1.18 (d, J=7 Hz, 3H); MS ESI (m/z) calcd. for $C_{32}H_{52}N_5O_{10}$ [M+H]$^+$ 666, found 666; HPLC purity. 98.8%; Chiral purity. 100%.

Example 6

Synthesis of (9R,12R,15R)-Methyl15-amino-2,2,12,22,22-pentamethyl-4,11,14,20-tetraoxo-3,21-dioxa-5,10,13,19-tetraazatricosane-9-carboxylate, Compound 8, SEQ ID NO:8

H-D-Orn(Boc)-D-Ala-D-Orn(Boc)-OMe (8).

Into a solution of 7 (25.0 g, 37.6 mmol) in anhydrous THF (200 mL) was added Pd—C (2.5 g, 10% on activated charcoal; wet basis) under nitrogen atmosphere, and the resulting solution was agitated for 3 h at ambient temperature under hydrogen pressure (40 psi). Completion of the reaction was indicated by TLC (dipped in ninhydrin solution, dried and heating). The reaction mixture was passed through a pad of Celite, solid on the filter was washed with THF (200 mL), filtrate thus obtained was concentrated under reduced pressure to 8 (18.2 g; crude) as a black fluffy mass which was used without further purification.

Example 7

Synthesis of (9R,12R,15R,18R)-Methyl-18-(benzyloxycarbonylamino)-15-(3-(tert-butoxycarbonylamino)propyl)-2,2,12,25,25-pentamethyl-4,11,14,17,23-pentaoxo-3,24-dioxa-5,10,13,16,22-pentaazahexacosane-9-carboxylate, Compound 9, SEQ ID NO:13

Z-D-Orn(Boc)-D-Orn(Boc)-D-Ala-Orn(Boc)-OMe (9).

To a well-stirred solution of 8 (18.2 g; crude) in anhydrous THF (500 mL) at 0° C. was added 1 (15.0 g, 38.3 mmol) under nitrogen atmosphere, and the contents were stirred for 2 h at ambient temperature after which reaction was completed as indicated by TLC. To the flask, silicycle amine (10 g) was added, and stirring was continued at ambient temperature for another 16 h to strip off residual anhydride. Silicycle amine was filtered off and the filtrate was evaporated under reduced pressure to have a crude residue. Purification of the crude product was done by recrystallization from hot acetonitrile to produce 9 (27.0 g, 81%) as an off-white solid. $^1$H NMR (400 MHz, DMSO-$d_6$). δ 8.22 (d, J=7.1 Hz, 1H), 7.92 (m, 2H), 7.33 (m, 6H), 6.78 (m, 3H), 5.02 (s, 2H), 4.25 (m, 3H), 4.01 (m, 1H), 3.60 (s, 3H), 2.88 (m, 6H), 1.56 (m, 6H), 1.52 (m, 6H), 1.37 (s, 27H), 1.1 (d, J=7 Hz, 3H); $^{13}$C NMR (100 MHz, DMSO-$d_6$) δ 172.8, 172.7, 172.2, 171.5, 156.4, 156.0, 137.8, 128.8, 128.2, 128.1, 77.8, 65.8, 54.9, 52.4, 52.2, 48.2, 29.9, 29.8, 28.7, 26.5, 26.4, 18.6. MS ESI (m/z) calcd. for $C_{42}H_{70}N_7O_{13}$ [M+H]$^+$ 881, found 881; HPLC purity. 99%; Chiral purity. 99%.

Example 8

Synthesis of (7S,10R,13R)-Methyl 7-(((9H-fluoren-9-yl)methoxy)carbonylamino)-13-(3-(tert-butoxycarbonylamino)propyl)-10-methyl-2,8,11-trioxo-5-thia-3,9,12-triazatradecan-14-oate, Compound 11, SEQ ID NO:14

Fmoc-D-Cys(Acm)-D-Ala-D-Orn(Boc)-OMe (11).

Into a well-stirred solution of Fmoc-D-Cys(Acm)-OH (10; 12.1 g, 29.2 mmol) and 6 (12.0 g, 37.8 mmol) in anhydrous THF (250 mL) at 0° C. under nitrogen atmosphere were added EDCl. HCl (6.12 g, 31.9 mmol), 1-hydroxybenzotriazole (3.95 g, 29.2 mmol) and N,N-diisopropylethylamine (5.4 mL, 31.9 mmol). The contents were allowed to stir at ambient temperature for 16 h. After completion of the reaction (TLC), reaction contents were poured into ice-cold water (250 mL) with stirring, and the precipitated solid was filtered and solid cake on the filter was washed with cold-water and dried in vacua to get a crude residue, which upon purification by silica-gel (230-400 mesh) flash column with 3% MeOH/CHCl$_3$ produced 11 (12.5 g, 66%) as a white solid. $^1$H NMR (300 MHz, DMSO-$d_6$). δ 8.60 (m, 1H), 8.22 (m, 1H), 7.91 (m, 3H), 7.71 (m, 2H), 7.59 (m, 1H), 7.40 (m, 2H), 7.30 (m, 2H), 6.78 (bs, 1H), 4.38-4.18 (m, 9H), 3.58 (s, 3H), 2.87 (m, 3H), 2.66 (m, 1H), 1.89 (s, 3H), 1.55 (m, 2H), 1.44 (m, 2H), 1.41 (s, 9H), 1.23 (d, J=7 Hz, 3H); $^{13}$C NMR (100 MHz, DMSO-$d_6$). δ 172.8, 172.7, 170.6, 170.4, 156.5, 156.0, 144.2, 141.2, 128.9, 127.5, 125.7, 120.5, 77.8, 66.2, 65.4, 54.8, 52.2, 48.4, 47.0, 32.9, 28.7, 28.6, 26.3, 23.01, 18.6, 15.6; MS ESI calcd. for $C_{35}H_{48}N_5O_9S$ [M+H]$^+$ 714.8, found 495; HPLC purity. 93.6%.

Example 9

Synthesis of (7S,10R,13R)-Methyl 7-acetamido-13-(3-(tert-butoxycarbonylamino)propyl)-10-methyl-2,8,11-trioxo-5-thia-3,9,12-triazatetradecan-14-oate, Compound 12, SEQ ID NO:15

Ac-D-Cys(Acm)-D-Ala-D-Orn(Boc)-OMe (12).

Piperidine (2.5 mL, 25.2 mmol) was added into a well-stirred suspension of 11 (12.0 g, 16.8 mmol) in anhydrous THF (250 mL) at 0° C. under nitrogen atmosphere and the resulting mixture was allowed to stir at ambient temperature. Reaction was completed after 16 h as indicated by TLC. Excess solvent was removed under reduced pressure to get a crude mass. The crude mass thus obtained was purified by basic alumina flash column with 3% MeOH/CHCl$_3$ to afford 6.5 g of the free amine intermediate. The amine (6.5 g) was taken in anhydrous THF (250 mL) and the reaction contents were cooled to 0° C. and to the flask were added acetyl chloride (1.1 mL, 15.8 mmol) and N,N-diisopropylethylamine (3.7 mL, 15.8 mmol) and stirring continued for 16 h, after which time reaction was found complete as indicated by TLC. The reaction mixture was poured into ice-water (250 mL) and crude product was extracted with EtOAc (2×300 mL). Combined organic layers were washed with brine, dried (anhydrous Na$_2$SO$_4$), filtered and the filtrate was evaporated under reduced pressure to get a crude residue, which upon purification by silica-gel (60-120 mesh) column with 3% MeOH/CH$_2$Cl$_2$ furnished 12 (6.0 g, 85%) as a white solid. $^1$H NMR (300 MHz, DMSO-$d_6$). δ 8.51 (m, 1H), 8.13 (t, J=9.6 Hz, 2H), 7.94 (d, J=7.5 Hz, 1H), 6.78 (bs, 1H), 4.47 (m, 1H), 4.35-4.09 (m, 4H), 3.58 (s, 3H), 2.85 (m, 3H), 2.58 (m, 1H), 1.83 (s, 6H), 1.67-1.52 (m, 3H), 1.36 (m, 1H), 1.35 (s, 9H), 1.20 (d, J=6.8 Hz, 3H); $^{13}$C NMR (100 MHz, DMSO-$d_6$). δ 172.8, 172.7, 170.5, 170.3, 169.9, 156.0, 77.9, 52.7, 52.2, 48.4, 33.0, 28.7, 28.6, 26.3, 23.0, 22.9, 18.6; MS ESI (m/z) calcd. for $C_{22}H_{40}N_5O_8S$ [M+H]$^+$ 533.8, found 533.8; HPLC purity. 99.9%.

Example 10

Synthesis of (7S,10R,13R)-7-Acetamido-13-(3-(tert-butoxycarbonylamino)propyl)-10-methyl-2,8,11-trioxo-5-thia-3,9,12-triazatetradecan-14-oic Acid, Compound 13, SEQ ID NO:3

Ac-D-Cys(Acm)-D-Ala-D-Orn(Boc)-OH (13).

To a well-stirred solution of 12 (6.0 g, 11.64 mmol) in a mixture of 1:1 THF and water (20 mL) was added 1N LiOH (13.5 mL, 13.5 mmol) at 0° C., and resulting solution was allowed to stir at the same temperature for 4 h. After the completion of the reaction as indicated by TLC, pH of the reaction mixture was lowered to pH-3 and aqueous phase was extracted with EtOAc three times (3×300 mL). Combined organic layers were washed with brine, dried (anhydrous Na$_2$SO$_4$), filtered and the filtrate thus obtained was evaporated under reduced pressure to get a crude residue, which upon purification by silica-gel (60-120 mesh) column with 5% MeOH/CH$_2$Cl$_2$ afforded 13 (3.5 g, 60%) as a off-white solid. $^1$H NMR (400 MHz, DMSO-d$_6$). δ 12.54 (bs, 1H), 8.53 (t, J=5.7 Hz, 1H), 8.11 (d, J=8.1 Hz, 1H), 8.01 (dd, J=21.5, 7.5 Hz, 2H), 6.80 (bs, 1H), 4.51 (m, 1H), 4.35 (m, 2H), 4.15 (m, 2H), 2.89 (m, 3H), 2.60 (m, 1H), 1.86 (s, 3H), 1.85 (s, 3H), 1.68 (m, 1H), 1.54 (m, 1H), 1.38 (m, 2H), 1.37 (s, 9H), 1.23 (d, J=7 Hz, 3H); $^{13}$C NMR (100 MHz, DMSO-d$_6$). δ 173.8, 172.5, 170.5, 170.3, 169.9, 156.0, 77.9, 60.2, 52.6, 52.2, 48.4, 33.0, 30.8, 28.8, 28.7, 26.5, 23.0, 22.9, 21.5, 21.2, 18.6; MS ESI (m/z) calcd. for C$_{21}$H$_{38}$N$_5$O$_8$S [M+H]$^+$ 519.8, found 519.8; HPLC purity. 99.9%.

Example 11

Synthesis of (9R,12R,15R,18R)-Methyl 18-amino-15-(3-(tert-butoxycarbonylamino)propyl)-2,2,12,25,25-pentamethyl-4,11,14,17,23-pentaoxo-3,24-dioxa-5,10,13,16,22-pentaazahexacosane-9-carboxylate, Compound 14, SEQ ID NO:2

H-D-Orn(Boc)-D-Orn(Boc)-D-Ala-Orn(Boc)-OMe (14).
Into a solution of Z-D-Orn(Boc)-D-Orn(Boc)-D-Ala-Orn(Boc)-OMe (9; 1.5 g) in anhydrous THF (35 mL) was added Pd—C (200 mg, 10% on activated charcoal; wet basis) under nitrogen atmosphere and the resulting solution was agitated for 4 h at ambient temperature under hydrogen pressure (40 psi). Completion of the reaction was indicated by TLC (dipped in ninhydrin solution, dried and heating). The reaction mixture was passed through a pad of Celite, solid on the filter was washed with THF (20 mL), filtrate thus obtained was concentrated under reduced pressure to furnish 14 (1.2 g; crude) as a black fluffy mass, which was used immediately without further purification in the next step.

Example 12

Synthesis of (7S,10R,13R,16R,19R,22R,25R)-Methyl 7-acetamido-13,16,19-tris(3-(tert-butoxycarbonylamino)propyl)-10,22,32,32-tetramethyl-2,8,11,14,17,20,23,30-octaoxo-31-oxa 5-thia-3,9,12,15,18,21,24,29-octaazatritriacontane-25-carboxylate, Compound 15, SEQ ID NO:4

Ac-D-Cys(Acm)-D-Ala-D-Orn(Boc)-D-Orn(Boc)-D-Orn(Boc)-D-Ala-Orn(Boc)-OMe (15).
Into a well-stirred solution of 14 (6.5 g, 7.41 mmol) in N-Methylpyrrolidone (100 mL) at 0° C. were added EDC.HCl (1.55 g, 8.08 mmol), N-hydroxy-5-norbornene-2,3-dicarboximide, HONb (1.2 mg, 6.74 mmol) and N,N-diisopropylethylamine (1.4 mL, 8.08 mmol) and the resulting solution was stirred at ambient temperature for 16 h, by which time a complete conversion of starting materials was indicated by TLC. The reaction contents were poured into ice-cold water (150 mL) with stirring, and the precipitated solid was filtered and solid cake on the filter was washed with cold-water and dried in vacua to get a crude residue, which upon purification by silica-gel (230-400 mesh) flash column with 6% MeOH/CHCl$_3$ produced 15 (5.2 g, 62%) as an off-white solid. $^1$H NMR (400 MHz, DMSO-d$_6$). δ 8.51 (t, J=5.9 Hz, 1H), 8.17 (dd, J=21.4, 7.44 Hz, 2H), 8.02 (d, J=7.5 Hz, 1H), 7.89 (m, 3H), 7.84 (d, J=7.8 Hz, 1H), 6.79 (m, 1H), 6.74 (m, 3H), 4.48 (m, 1H), 4.29 (m, 4H), 4.13 (m, 4H), 3.62 (s, 3H), 2.88 (m, 6H), 2.71-2.49 (m, 4H), 1.86 (s, 6H), 1.61 (m, 8H), 1.38 (m, 8H), 1.37 (s, 36H), 1.2 (m, 6H); MS ESI (m/z) calcd. for C$_{55}$H$_{99}$N$_{12}$O$_{18}$5 [M+H-Boc]$^+$ 1147.6, found 1147.6; HPLC purity. 99%; Chiral purity. 97%.

Example 13

Synthesis of 7S,10R,13R,16R,19R,22R,25R)-7-Acetamido-13,16,19-tris(3-(tert-butoxycarbonylamino)propyl)-10,22,32,32-tetramethyl-2,8,11,14,17,20,23,30-octaoxo-31-oxa-5-thia-3,9,12,15,18,21,24,29-octaazatritriacontane-25-carboxamide, Compound 16, SEQ ID NO:16

Ac-D-Cys(Acm)-D-Ala-D-Orn(Boc)-D-Orn(Boc)-D-Orn(Boc)-D-Ala-Orn(Boc)-NH$_2$ (16).
To a well-stirred solution of 15 (5.0 g, 4.05 mmol) in anhydrous MeOH (200 mL) at 0° C. was bubbled NH$_3$(g) for 1 h through a needle adopter and ammonia purging was continued at interval of every 12 h for 48 h. Stirring was continued until in-process sample indicated the complete disappearance of starting material. Excess solvent was removed under reduced pressure to get a crude mass, which was washed with diethyl ether (100 mL) to get a solid. Further purification of the crude solid by silica-gel (60-120 mesh) column with 7% MeOH/CHCl$_3$ yielded 16 (3.6 g, 73%) as an off-white solid. $^1$H NMR (400 MHz, DMSO-d$_6$). δ 8.49 (t, J=6.5 Hz, 1H), 8.13 (d, J=7.8 Hz, 1H), 8.01 (m, 1H), 7.92 (m, 3H), 7.81 (d, J=7.6 Hz, 1H), 7.70 (d, J=7.4 Hz, 1H), 7.24 (bs, 1H), 7.00 (s, 1H), 6.72 (m, 4H), 4.47 (m, 1H), 4.34-4.10 (m, 8H), 2.87 (m, 6H), 2.60 (m, 4H), 1.86 (s, 6H), 1.65 (m, 8H), 1.36 (m, 8H), 1.34 (s, 36H), 1.23 (m, 6H)); MS ESI (m/z) calcd. for C$_{54}$H$_{98}$N$_{13}$O$_{17}$S [M+H]$^+$ 1233.6, found 1233.6; HPLC purity. 96.3%. Chiral purity. 98%.

Example 14

Synthesis of (R)-2-((7S,10R,13R,16R)-7-acetamido-13,16-bis(3-aminopropyl)-10-methyl-2,8,11,14-tetraoxo-5-thia-3,9,12,15-tetraazaheptadecanamido)-5-amino-N—((R)-1-((R)-1,5-diamino-1-oxopentan-2-ylamino)-1-oxopropan-2-yl)pentanamide, Compound 17, SEQ ID NO:17

Ac-D-Cys(Acm)-D-Ala-D-Orn-D-Orn-D-Orn-D-Ala-Orn-N H$_2$ (17).
Into a stirred solution of 16 (1.5 g, 1.21 mmol) in 5N HCl in EtOAc, 15 mL) was added triisopropyl silane (1.2 mL, 6.0 mmol) at 0° C. at ambient temperature under nitrogen atmosphere. Completion of Boc-deprotection occurred by 1 h as indicated by LCMS analysis of the in-process sample. Excess solvent was decanted and solid residue was washed with diethyl ether to get the crude amine, which was taken to the next step without further purification. MS ESI (m/z) calcd. for C$_{34}$H$_{66}$N$_{13}$O$_9$S [M+H]$^+$ 832.8, found 832.8.

Example 15

Synthesis of Ac-D-Cyst(Acm)-D-Ala-[D-Arg(di-tert-butylcarboxyguaninyl)$_3$]-D-Ala-D-Arg(di-tert-butylcarboxyguaninyl)-NH$_2$, Compound 18, SEQ ID NO:18

Ac-D-Cyst(Acm)-D-Ala-D-Arg(Boc)$_2$-D-Arg(Boc)$_2$-D-Arg(Boc)$_2$-D-Ala-D-Arg(Boc)$_2$-NH$_2$ (18).
To a well-stirred solution of crude 17 (920 mg) in a mixture of MeOH (8 mL) and water (2 mL) were added (Z)-tert-butyl (1H-pyrazol-1-yl)methylenedicarbamate (2.06 g, 6.63 mmol) and N,N-diisopropylethylamine (3.8 mL, 22.13 mmol) at ambient temperature and the contents were stirred for 12 h at ambient temperature, after which time completion of the reaction was indicated by LCMS analysis of the in-process sample. Excess solvents were removed under reduced pressure to get a crude material, which was dissolved in EtOAc (300 mL) and the solution was washed with cold water and brine, dried (anhydrous $Na_2SO_4$), filtered and the filtrate thus obtained was concentrated under reduced pressure to get a crude mass, purification of which by silica-gel (230-400 mesh) flash column with 70% EtOAc/petroleum ether afforded 18 (680 mg, 31%) as an off-white solid. $^1$H NMR (400 MHz, DMSO-$d_6$). δ 11.50 (s, 4H), 8.50 (t, J=6.4 Hz, 1H), 8.27 (m, 4H), 8.13 (d, J=8 Hz, 1H), 8.06-7.95 (m, 5H), 7.74 (d, J=7.9 Hz, 1H), 7.29 (s, 1H), 7.05 (s, 1H), 4.46 (m, 1H), 4.34-4.12 (m, 8H), 3.26 (m, 8H), 2.85 (m, 1H), 2.65 (m, 1H), 1.86 (s, 6H), 1.65 (m, 8H), 1.50 (m, 8H), 1.46 (s, 36), 1.39 (s, 36H), 1.21 (m, 6H); MS ESI calcd. for $C_{78}H_{138}N_{21}O_{25}S$ $[M+H]^+$ 1801.1, found 1801.6; HPLC purity. 94.9%; Chiral purity. 98%.

Example 16

Synthesis of Etelcalcetide, Compound 20

Etelcalcetide.

To a suspension if 18 (0.180 g, 0.1 mmol) in DCM (2.0 mL) in a vial at 20° C. was added TFA (2.0 mL) and the contents aged overnight (contents became homogeneous solution). The LCMS indicated completion of reaction (m/2=500.2) was observed by mass spectrometry. The reaction mixture was subjected to reduced pressure distillation to afford an oily residue which was dissolved in water and lyophilized to afford the TFA salt of product 19 (SEQ ID NO:5) as a foam (0.163 g). Theoretical amount of TFA salt is 0.147 g and the extra mass is likely due to the water (hygroscopic) which is still present in the lyophilized cake. This material was used in the next step without further purification. To a suspension of TFA salt of penultimate 19 (0.068 g, 0.068 mmol) in MeOH 1 mL was added 1 mL DI water and the contents aged to form a solution (some particles still insoluble even after prolonged sonication). To this mixture, Cysteine hydrochloride hydrate (0.015 g, 1.25 equiv) and Iodine (0.022 g, 1.25 equiv) were added and the contents sonicated to dissolve iodine. The contents were aged at room temperature and monitored by LC-MS (50 uL diluted to 1 mL using 1/1 water/ACN). The 10 min sample did not show any product formation, samples at 1 h 3 h and 4 h showed formation of product as doubly charged ion along with the presence of starting material. The contents were aged overnight and the data analysis on the sample showed still some starting material present in the mixture. To the contents Amberlite IRN (Cl form) resin was added and aged for 1 h. Most of the brownish color went to the resin and the contents filtered through a fine frit to afford a colorless solution which was lyophilized to afford brown residue. The formation of etelcalcetide (20) was confirmed by LC-MS as a major product. The product was not further purified.

Example 17

Preparation of Z-D-Ala-OSu (22)

Z-D-Ala-OSu (22).
51.8 g of Z-(D)Ala-OH and 30.3 g of SucOH (1.05 eq) 21 were dissolved in 560 ml acetonitrile and the solution cooled to 0° C. 54.6 g of DCC (1.1 eq) dissolved in 80 ml acetonitrile and slowly added. Thirty min after the addition the solution was brought to room temperature. After overnight aging the conversion was >99% by HPLC. The DCU by-product was removed by filtration and washed the cake with acetonitrile (2×250 ml). The filtrate and washings were combined and concentrated under vacuum to afford a solution weighing 573 g. To this solution was added 1920 ml iPrOH and the mixture was cooled at 4° C. overnight. The obtained crystals were filtered-off and washed with IPA (2×165 mL). After overnight drying 65 g of 22 was isolated (HPLC purity: 100% RS (chromatogram below), yield: 85%).

Example 18

Preparation of H-D-Ala-D-Arg-$NH_2$. 2HCl (25)

H-D-Ala-D-Arg-$NH_2$. 2HCl (25).
To a suspension of H-(D)Arg-$NH_2$ (19.4 g, 75 mmol) 23 in 350 ml dimethylacetamide, 9.7 g of DIPEA (1 eq) was added followed by Z-(D)Ala-OSu 22 (27.5 g, 1.1 eq, 82.5 mmol) at RT. After 1.5 h a conversion of 95% was obtained and the mixture diluted with 1120 ml water. This solution was washed twice with 625 ml ethyl acetate in order to remove Z-(D)Ala-OSu and Z-(D)Ala-OH (formed by hydrolysis of the activated ester). The pH of the resulting aqueous phase was adjusted to 10.88 using $Na_2CO_3$ (28.1 g, 3.54 eq) and 29 g of sodium tetraphenylborate (NaTPB) (1.1 eq) was added. This lead to a gummy precipitation that was dissolved upon addition of 1250 ml dichloromethane. This allows selective extraction of the formed dipeptide in the organic phase as TPB salt. The resulting aqueous phase was re-extracted twice with 500 ml dichloromethane after addition of 7.2 and 2.4 g NaTPB. In the final aqueous phase, 1.3% of product was lost (estimated by HPLC). The organic phases were combined and concentrated to a volume of 1500 ml and then washed twice by 1100 ml water. The washed organic layer was concentrated and a solvent exchange to methanol was performed to obtain a solution of 308 g. The solid formed during concentration (salts of TPB, do not contain peptide according to HPLC analysis) was removed by filtration. In the next step the solution was treated with a strong basic anion exchange resin (Amberlite IRA 958 Cl form) in order to exchange tetraphenylborate into chloride. This was done partially in a batch reaction and on a glass column. In total, 676 g (9 eq) of resin was necessary to remove the tetraphenylborate (monitored by HPLC). The resin was washed with methanol to recover the peptide. The obtained solution was concentrated to 360 g containing Z-(D)Ala-(D)Arg-$NH_2$ 24 in solution (93.8 Area % by HPLC).

To this solution was added 8 g Pd/C paste (5%) and hydrogen gas bubbled through the solution at RT. After 4 h the deprotection was found to be complete. The catalyst was filtered-off and 19.7 g HCl 4N in dioxane (1 eq) added before the solution is concentrated under vacuum. Once the methanol was removed the residual water (coming from residual water present on the anion-exchange resin) is eliminated through azeotropic distillation with acetonitrile (addition in fed batch, a total ca. 2 L). During drying a solid was formed, initially gummy, when dried further it became crystalline. The solid was isolated by filtration and dried under vacuum at 45° C. 19.7 g of 25 was obtained (yield 71.9%).

Example 19

Synthesis of H-D-Arg-D-Ala-D-Arg-NH$_2$.2HCl (28)

H-D-Arg-D-Ala-D-Arg-NH$_2$.2HCl (28).

To a suspension of Z-D-Arg-OH, 26 (16.15 g, 52.7 mmol) in 170 ml DMAc at RT was added 13.7 g of HCl 4N in dioxane (1 eq, 52.7 mmol). This clear solution was cooled to −15° C. under N$_2$ atmosphere and during cooling 6.8 g of DIPEA (1 eq) and 4.2 g of pyridine (1 eq) were added. Activation was done by addition of pivaloyl chloride (6.32 g, 52.7 mmol, 1 eq). After 5 min of activation a solution of 25 (19.1 g, 52.7 mmol, 1 eq) in 132 ml DMAc with 6.5 g DIPEA (0.97 eq as determined by titration) cooled to 0° C. was added. The reaction mixture was allowed to warm to RT and after 30 minutes the reaction was considered complete. The mixture was diluted with 780 ml demineralised water containing 14.7 g sodium carbonate (3.54) to reach a pH of 10.6. 40.63 g of sodium tetraphenylborate (NaTPB) (2.2 eq) was added. This lead to a gummy precipitation that was dissolved by addition of 870 ml dichloromethane. This allowed selective extraction of the formed tripeptide in the organic phase as TPB salt. The resulting aqueous phase re-extracted once with 400 ml dichloromethane after addition of 12.6 g NaTPB. In the final aqueous phase, 2.5% of product was lost (estimated by HPLC). The organic phases were combined and concentrated to a volume of 1000 ml and then washed twice with 750 ml water. The washed organic layer is concentrated and a solvent exchange to methanol was performed to obtain a solution of 198 g. The solid formed during concentration (salts of TPB, do not contain peptide according to HPLC analysis) was removed by filtration. Here, the ion-exchange was performed by addition of 17 g benzyltriethylammonium chloride (1.4 eq) at 0° C. The formed benzyltriethylammonium tetraphenylborate precipitates in methanol and the chloride salts of the peptides stay in solution. After filtration the solid is washed with 130 ml methanol. The mother liquors are concentrated to obtain a solution of 419 g. In order to remove the TPB that has not been precipitated as quaternary ammonium salt (about 10%) the solution was treated with 520 g (10 eq) Amberlite IRA 958Cl. The resin was washed with methanol to recover the peptide. The obtained solution was concentrated to 419 g containing 27. To this solution, 2.8 g Pd/C paste (5%) was added and hydrogen gas bubbled through the solution at RT. After 1 h the catalyst was filtered-off and the mother liquors concentrated under vacuum. Once the methanol was removed the residual water (coming from residual water present on the anion-exchange resin) was removed through azeotropic distillation with acetonitrile (addition in fed batch, a total ca. 1.1 L). During drying a solid was formed, initially gummy, when dried further crystalline. The solid was isolated by filtration and dried under vacuum at 45° C. 17.22 g of powder were obtained (HPLC purity 95.5% RS, yield 53%).

Example 20

Synthesis of H-(D)Arg-(D)Arg-(D)Ala-(D)Arg-NH$_2$.4HCl (30) (SEQ ID NO:10)

H-(D)Arg-(D)Arg-(D)Ala-(D)Arg-NH$_2$.4HCl (30).

H-(D)Arg-(D)Ala-(D)Arg-NH2.2HCl, 28 (16.6 g, 27 mmol) and Z-Arg-OH, 26 (9.6 g, 30.5 mmol, 1.13 eq) were suspended in 285 ml DMA and 4N HCl in dioxane (5.4 g, 0.77 eq as determined by titration of the tripeptide) was added along with 4.2 g of HOBt. The suspension was heated to 40° C. to obtain a solution that was subsequently cooled to 0° C. Ethyldiisopropylcarbodiimide hydrochloride (EDC) (5.96 g, 1.14 eq) was added in two portions over 30 min. Once the EDC was solubilised the solution was allowed to warm to RT and aged overnight. A conversion of >90% was reached and the solution was diluted with 400 ml demineralised water containing 10.1 g sodium carbonate (3.54 eq) to reach a pH of 10.88. Sodium tetraphenylborate (NaTPB) (29.6 g, 3.1 eq) was added. This lead to a gummy precipitation that was dissolved by adding 450 mL dichloromethane. This allowed selective extraction of the formed tetrapeptide in the organic phase as TPB salt. The resulting aqueous phase was re-extracted once with 200 ml dichloromethane after addition of 2.1 g NaTPB. In the final aqueous phase, 3% of product was lost (estimated by HPLC). The organic phases were combined and washed twice with 400 ml water. The washed organic layer was concentrated and a solvent exchange to methanol performed to obtain a solution of 193 g. The solution was treated with 715 g (26 eq) Amberlite IRA 958 Cl form resin. The resin was washed with methanol to recover the peptide. The obtained solution was concentrated to 248 g of a solution containing 29 (Z-D-Arg-D-Arg-D-Ala-D-Arg-OH.2HCl, SEQ ID NO:12). To this solution 2.9 g Pd/C paste (5%) was added and hydrogen gas bubbled through the solution at RT. After 1 h the deprotection was complete and the catalyst filtered-off and the filtrate concentrated under vacuum followed by the addition of 7 g HCl 4N in dioxane (1 eq). Once the methanol was removed the residual water (coming from residual water present on the anion-exchange resin) was removed through azeotropic distillation with acetonitrile (addition in fed batch, a total ca. 1.1 L). During drying solid was formed, initially gummy, when dried further crystalline. The solid is isolated by filtration and dried under vacuum at 45° C. 18.1 g of 30 was obtained (HPLC purity 94.1% RS (chromatogram below) in 74.5% yield, sample sent to CAT for enantiomeric purity).

Example 21

Synthesis of Z-D-Ala-D-Arg-OH.HCl (32)

Z-D-Ala-D-Arg-OH.HCl (32).

H-(D)Arg-OH, 31 (9.6 g, 55 mmol) was dissolved in 160 ml demineralised water and Z-(D)Ala-OSu, 22 (19.9 g, 1.1 eq) was dissolved in 292 ml acetonitrile separately. The latter solution was added to the former at RT. Once the active ester was consumed (coupling or hydrolysis), the reaction mixture was diluted with 100 ml demineralised water and acetonitrile removed by distillation under vacuum to obtain a solution of 320 g. The solution was acidified with 1.2N HCl to pH 2.5 and washed twice with 275 ml EtOAc (to remove Z-D-Ala-OH). Subsequently the peptide was extracted from the aqueous phase with respectively 285, 275 and 220 ml 2-BuOH. The organic layers were combined and concentrated under vacuum and dried through azeotropic distillation. In total 2.5 L of 2-BuOH was added in feed batch. To the concentrated solution (121 g) was added 437 ml of isopropyl acetate to cause precipitation. The solid was filtered and triturated twice with 220 ml iPrOAc in order to eliminate as much as possible the liberated SucOH. Finally, the solid was re-dissolved in 100 ml iPrOH and precipitated in 500 ml diisopropylether to obtain a solid. After filtration and washing with 100 ml diisopropylether the solid was dried under vacuum to afford 18 g of 32 (HPLC purity: 98.3% (chromatogram below), yield 73%).

Example 22

Synthesis of H-D-Ala-D-Arg-OH.HCl (33)

H-D-Ala-D-Arg-OH.HCl (33).

Z-D-Ala-D-Arg-OH 32 (18 g, 38 mmol) was dissolved in 230 ml MeOH+75 ml water. 2.5 g of Pd/C-paste (5%) was added and hydrogen gas is bubbled through the solution at RT. After 1.5 h the deprotection reaction was complete and the catalyst removed by filtration on a 0.45p filter and washed with 46 ml MeOH. The peptidic solution was concentrated under vacuum and the water is removed by azeotropic distillation by addition of acetonitrile in feed batch (4×250 ml). During the distillation the deprotected dipeptide falls out. Finally the obtained suspension is concentrated to 189 g and filtered-off and washed with acetonitrile. After overnight drying at 45° C., 11.2 g of white powder is obtained (HPLC purity 97.4% RS (chromatogram below), yield: 91.3%).

Example 23

Synthesis of Fmoc-D-Cys(Trt)-D-Ala-D-Arg-OH.HCl (35), SEQ ID NO:19

Fmoc-D-Cys(Trt)-D-Ala-D-Arg-OH.HCl (35), SEQ ID NO:19.

Fmoc-D-Cys(Trt)-OH 34 (9.6 g, 1.0 eq) and HONb (N-hydroxynorbornene) (3.2 g, 1.05 eq) were dissolved in 14 ml of DMF at RT. This mixture was diluted with 50 ml iPrOAc and cooled to 0° C. Dicyclohexylcarbodiimide (DCC, 3.7 g) was dissolved in 4 ml iPrOAc and was added to the solution containing Fmoc-D-Cys(Trt)-OH. Once the DCC added, the reaction mixture was allowed to warm to RT and stirred for 2 h. After 2 h (conversion rate >96%) the DCU was removed by filtration and washed with 20 ml iPrOAc. To this solution was added a solution of H-(D)Ala-(D)Arg-OH 33 (6.0 g, 1.1 eq) and DIPEA (2.4 ml, 1.09 eq) in 40 ml DMF and 24 ml demineralised water at RT. After overnight reaction the Fmoc-(D)Cys(trt)-ONb was completely consumed and the mixture diluted with 200 ml iPrOAc, 200 ml water and 200 ml dichloromethane. After phase separation the aqueous phase was discarded and the organic phase washed with 350 ml demineralised water followed by a 2 (w/v) % NaCl solution. The organic layer concentrated under vacuum and a solid appeared upon the removal of dichloromethane. This solid was filtered and HPLC showed Fmoc-(D)Cys(trt)-OH as major impurity. When repeating the precipitation procedure 3× it was possible to reduce the content to ca. 2%. After drying 13.9 g of solid was obtained (HPLC purity 95% RS (chromatogram below), yield 96%).

Example 24

Synthesis of Ac-D-Cys(Trt)-D-Ala-D-Arg-OH (36), SEQ ID NO:9

Ac-D-Cys(Trt)-D-Ala-D-Arg-OH (36), SEQ ID NO:9.

Fmoc-D-Cys(trt)-D-Ala-D-Arg-OH.HCl (35) (8.65 g, 9.8 mmol, 1.0 eq) was suspended in 80 ml of MeOH and piperidine (6.8 g, 8 eq) was gradually added at RT. Once the conversion rate was >97% the solution was added to 600 ml methylterbutylether (MTBE). The precipitate was filtered-off, washed with 80 ml MTBE and dried overnight under vacuum at 45° C. 6.2 g of H-D-Cys(trt)-D-Ala-D-Arg-OH (Compound 38) was obtained as a white powder was obtained. (94.5% RS (HPLC method 1, chromatogram below), yield: 95.4%).

H-D-Cys(trt)-D-Ala-D-Arg-OH 38 (6.0 g, 9.1 mmol, 1.0 eq) was dissolved in 75 ml of dichloromethane. 792 µl 4N HCl in dioxane (0.348 eq as determined by titration) was added followed by 3.4 g of acetyl-N-hydroxysuccinimide (AcOSu) (2.4 eq) added in 3 portions at RT. In order to accelerate the reaction the pH was increased from 3.5 to 6 by the addition of DIPEA. This caused gelification of the peptide (most probably the zwitterionic form is not soluble in dichloromethane). A solution was obtained after addition of 15 ml of dimethylacetamide (DMAc) and removal of dichloromethane. The reaction was continued until a conversion rate of 98% was obtained (48 h) and then precipitated with 350 ml iPrOAc. The solid was filtered and washed with 85 ml of iPrOAc. The solid was taken up in 90 ml MeOH and precipitated again in 200 ml iPrOAc. After filtration the solid was dried overnight under vacuum at 45° C. to afford 36 (5 g) as white powder (98.2% RS (HPLC method 1, 87.3% yield). HPLC Conditions Corresponding to HPLC Method 1: Column: Merck Chromolith RP C18-e (100 mm×4.6 mm) Mobile phase A: water 0.1% TFA Mobile phase B: acetonitrile 0.1% TFA Column temperature: 40° C. Flow: 4 ml/min UV at 220 nm Gradient: start at 2% B, from 2 to 73.3% B in 8 min.

Example 25

Synthesis of Ac-D-Cys(Trt)-D-Ala-D-Arg-D-Arg-D-Arg-D-Ala-D-Arg-NH$_2$. 4HCl (37), SEQ ID NO:11

Ac-D-Cys(Trt)-D-Ala-D-Arg-D-Arg-D-Arg-D-Ala-D-Arg-N H$_2$. 4HCl (37), SEQ ID NO:11.

Ac-(D)-Cys(trt)-D-Ala-D-Arg-OH, 36 (7.9 g, 12.0 mmol), H-D-Arg-D-Arg-D-Ala-D-Arg-NH$_2$.4HCl, 30 (11.0 g, 1.005 eq) and HOPO (2-Hydroxypyridine-N-oxide, 1.40 g, 1.05 eq) were suspended in 130 ml DMA and stirred until dissolution (overnight). Once a solution, the reaction mixture was cooled on an ice bath and 2.4 g EDC.HCl (1.03 eq) was added. After 8 h of reaction, 78 µl of DIPEA (0.1 eq) were added to accelerate the reaction. 24 h after the initiation of the reaction, the temperature was raised to 20° C. 382 µl of DIPEA (0.2 eq) were added in two portions as well as 117 mg EDC.HCl (0.05 eq) to terminate the reaction. Once a conversion rate of 96% obtained (48 h) the peptide was precipitated in 1100 ml acetonitrile, filtered-off and washed with 1250 ml acetonitrile. After overnight drying under vacuum at 45° C., 17.3 g of crude 37 as white powder was obtained. (86.7% RS (HPLC method 2). HPLC Method 2 Conditions: Column: Zorbax SB-C18 (150 mm×4.6 mm, 3.5μ) Mobile phase A: water 20 mM pentafluoropropionic acid (PFPA) Mobile phase B: acetonitrile 20 mM pentafluoropropionic acid (PFPA) Column temperature: 40° C. Flow: 1.5 ml/min UV at 220 nm Gradient: start at 2% B, from 2 to 91.1% B in 20 min. The crude peptide was purified by preparative scale reverse phase HPLC to afford 64% of desired peptide in greater than 99 Area % by HPLC. HPLC conditions: Column: Daisopak SP-120-25-ODS-RPS 20×250 mm, Mobile phase A: 1% HOAc in water, Mobile phase B: 1% HOAc in acetonitrile, Flow rate: 19 ml/min, Gradient: 5% B for 1 min, 5-25% B in 20 min, 25-90% B in 1 min, wash at 90% B for 5 min, Sample: 42 g/L Ac-(D)Cys(trt)-(D)Ala-(D)Arg-(D)Arg-(D)Arg-(D)Ala-(D)Arg-NH2.4HCl at 88% RS HPLC purity, Injection volume: 3 ml Fractions of 0.75 min.

Example 26

Synthesis of Etelcalcetide (Compound 20)

Etelcalcetide.

Ac-(D)Cys(trt)-(D)Ala-(D)Arg-(D)Arg-(D)Arg-(D)Ala-(D)Arg-NH2.4HCl, 37, SEQ ID NO:11 (1.0 g, 0.64 mmol) was dissolved in 95 ml water and H-Cys(trt)-OH (2.4 g, 10 eq) was added. The pH of the solution was adjusted to 2.85 by means of aqueous HCl and this aided in the dissolution of H-Cys(trt)-OH. A 2% solution of iodine in MeOH was added in portions (approximately every hour) until a total of about 10 eq were added. After overnight reaction the starting material was completely consumed and methanol and acetonitrile were removed by evaporation. The precipitated trityl derivatives (cleavage products) were removed by extraction with MTBE. The obtained aqueous solution (approximately 60 ml) containing crude etelcalcetide (at 5.9 g/L) was further purified (60% RS (HPLC method 2), yield 53% (estimated by HPLC assay). Following preparative chromatography, fractions were isolated and had a purity >95% RS (UPLC) with a yield >90%. UPLC Conditions: Column: Waters ACQUITY UPLC HSS T3 Column (100 Å, 1.8μ, 2.1×150 mm) Mobile phase A: 0.1% TFA in 3% acetonitrile Mobile phase B: 0.1% TFA in 30% acetonitrile Column temperature: 45° C. Flow: 0.25 ml/min UV at 220 nm Gradient: 0% B for 1 min, from 0 to 34% B in 23 min, from 34 to 70% B in 9 min.

It is claimed:

1. A method for preparing etelcalcetide or a precursor thereof, the method comprising:
   (i) coupling an N-terminal protected tetrapeptide fragment of etelcalcetide comprising D-ornithine in place of D-arginine with a protected tripeptide fragment of etelcalcetide in solution phase to form a protected heptapeptide precursor of etelcalcetide comprising a terminal D-cysteine.

2. The method of claim 1, wherein the tetrapeptide fragment of etelcalcetide has the structure, H-D-Orn(Boc)-D-Orn(Boc)-D-Ala-Orn(Boc)-OMe (Compound 14).

3. The method of claim 2, wherein the tetrapeptide fragment of etelcalcetide has the structure, H-D-Orn(Boc)-D-Orn(Boc)-D-Ala-Orn(Boc)-OMe (Compound 14).

4. The method of claim 2, wherein the tripeptide fragment has the structure Ac-D-Cys(Acm)-D-Ala-D-Orn(Boc)-OH (Compound 13), and the protected heptapeptide precursor of etelcalcetide has the structure Ac-D-Cys(Acm)-D-Ala-D-Orn(Boc)-D-Orn(Boc)-D-Orn(Boc)-D-Ala-Orn(Boc)-OMe (Compound 15).

5. The method of claim 4, wherein the tripeptide fragment is a solid at room temperature.

6. The method of claim 1, wherein the coupling is carried out in an organic solvent to provide a reaction mixture, the method further comprising adding water to the reaction mixture to precipitate the protected heptapeptide precursor of etelcalcetide.

7. The method of claim 1, further comprising: (ii) removing the δ-amino protecting group in ornithine from the protected heptapeptide precursor of etelcalcetide, and (iii) guanylating the deprotected heptapeptide precursor of etelcalcetide to thereby replace the ornithine residues with arginine to form an intermediate having the structure,

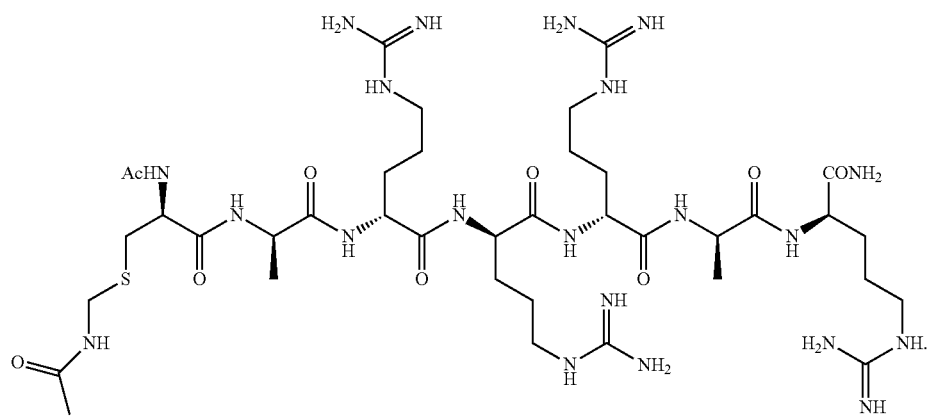

(Compound 19)

8. The method of claim 7, further comprising (iv) coupling the terminal D-cysteine of the intermediate formed in step (iii) with L-cysteine via formation of a disulfide bond to form etelcalcetide.

9. A method for preparing etelcalcetide or a pharmaceutically acceptable salt thereof, comprising (i) reacting the intermediate structure according to claim 7,

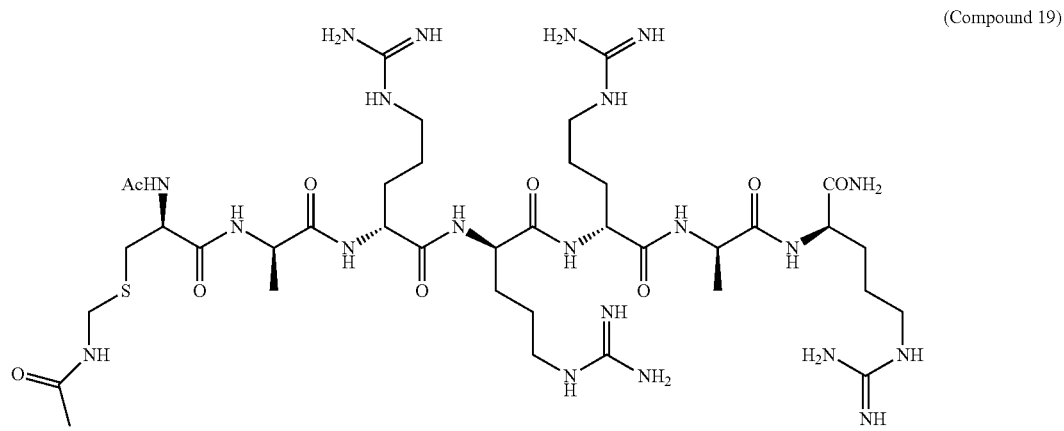 [SMILES: CC(=O)NCSC[C@@H](NC(C)=O)C(=O)N[C@H](C)C(=O)N[C@H](CCCNC(=N)N)C(=O)N[C@H](CCCNC(=N)N)C(=O)N[C@H](CCCNC(=N)N)C(=O)N[C@H](C)C(=O)N[C@H](CCCNC(=N)N)C(N)=O]

(Compound 19)

with L-cysteine in solution phase.

10. The method of claim 9, wherein the D-cysteine of Compound 19 comprises an acetamido protecting group, the method further comprising (ii) cleaving the acetamido protecting group.

11. The method of claim 10, wherein the reacting step (i) and the cleaving step (ii) are carried out in a single reaction vessel.

12. The method of claim 1, further comprising, prior to coupling step (i), (a) preparing in solution phase the N terminal protected tetrapeptide fragment of etelcalcetide.

13. The method of claim 12, wherein the N-terminal protected fragment tetrapeptide of etelcalcetide is prepared via a continuous solution phase process.

14. The method of claim 12, wherein the preparing step (a) comprises: (a-i) coupling a urethane protected N-carboxyanhydride of ornithine with a dipeptide having a structure

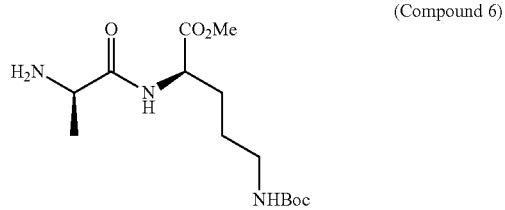 [SMILES: COC(=O)[C@@H](CCCNC(=O)OC(C)(C)C)NC(=O)[C@@H](C)N]

(Compound 6)

to form a protected tripeptide, (a-ii) deprotecting the tripeptide to form a deprotected tripeptide, and (a-iii) coupling the deprotected tripeptide to a urethane protected N-carboxyanhydride of ornithine to form the N-terminal protected tetrapeptide fragment of etelcalcetide.

15. The method of claim 14, wherein the preparing step results in formation of a gaseous by-product.

16. The method of claim 14, wherein the urethane-protected N-carboxyanhydride of ornithine is a benzyloxycarbonyl-protected N-carboxyanhydride of protected D-ornithine.

17. The method of claim 14, wherein each of the coupling steps (a-i) and (a-iii) is carried out in tetrahydrofuran.

18. The method of claim 12, wherein the solution phase comprises an organic solvent selected from the group consisting of ethers, esters, aromatic hydrocarbons, and chlorinated hydrocarbons.

19. The method of claim 1, further comprising purifying the tetrapeptide fragment of etelcalcetide by precipitation or recrystallization prior to coupling step (i).

* * * * *

UNITED STATES PATENT AND TRADEMARK OFFICE
CERTIFICATE OF CORRECTION

PATENT NO. : 10,858,389 B2
APPLICATION NO. : 15/561009
DATED : December 8, 2020
INVENTOR(S) : Sheng Cui et al.

Page 1 of 1

It is certified that error appears in the above-identified patent and that said Letters Patent is hereby corrected as shown below:

In the Claims

Replace Claim 3, as shown below:
3. The method of claim 2, wherein the f!>J terminal tetrapeptide fragment of
etelcalcetide has the structure, H-D-Orn{Boc)-D-Orn(Boc)-D-A la-Orn(Boc)- orv'le (Compound i 4).

Signed and Sealed this
Nineteenth Day of December, 2023

Katherine Kelly Vidal
*Director of the United States Patent and Trademark Office*